United States Patent [19]
Hottinger et al.

[11] Patent Number: 5,514,586
[45] Date of Patent: May 7, 1996

[54] PLASMID VECTORS AND GRAS MICROORGANISMS PROMOTING ICE NUCLEATION

[75] Inventors: Herbert Hottinger, Blonay; Peter Niederberger, Epalinges; David Pridmore, Pully, all of Switzerland; Ursula Staeger-Roos, Cheong Ju, Rep. of Korea

[73] Assignee: Nestec S.A., Vevey, Switzerland

[21] Appl. No.: 963,290

[22] Filed: Oct. 19, 1992

Related U.S. Application Data

[63] Continuation of Ser. No. 596,203, Oct. 11, 1990, abandoned.

[30] Foreign Application Priority Data

Oct. 25, 1989 [GB] United Kingdom .................. 8923998

[51] Int. Cl.$^6$ ........................ C12N 1/19; C12N 15/81; C12N 15/31; A23L 1/28
[52] U.S. Cl. .................. 435/254.21; 435/320.1; 536/23.7; 426/62
[58] Field of Search ...................... 435/69.1, 69.8, 435/71.1, 172.3, 252.3, 255, 252.33, 320.1, 942, 256, 254.21; 536/27, 23.7; 426/61, 62

[56] References Cited

U.S. PATENT DOCUMENTS

| | | | |
|---|---|---|---|
| 4,021,581 | 5/1977 | Sing | 426/61 |
| 4,200,228 | 4/1980 | Woerpel | 239/25 |
| 4,978,540 | 12/1990 | Lee | 426/61 |

FOREIGN PATENT DOCUMENTS

| | | | |
|---|---|---|---|
| 0340170A2 | 4/1989 | European Pat. Off. | C12N 15/00 |
| WO8303831 | 11/1983 | WIPO | C07H 21/04 |
| WO8906498 | 7/1989 | WIPO | A23L 3/36 |

OTHER PUBLICATIONS

Van de Guchte et al., Appl. & Environment. Microbiol., 55(1): 224–228 (Jan. 1989).
Green et al. "Physical and functional repetition in a bacterial ice nucleation gene" Nature 317:17 (1985) 645–648.
Warren, et al. "Conserved repeats in ice nucleation structural genes from two species of Pseudomonas" Nucleic Acids Research vol. 14, No. 20 (1986) pp. 8047–8060.
Bajwa, et al., "Structural analysis of the two tandemly repeated acid phosphatase genes in yeast" Nucleic Acids Research, 12:10 (1984) pp. 7721–7739.
Kurjan, et al. "Structure of a yeast Phermone Gene (MFα): A Putative α–Factor Precursor Contains Four Tandem Copies of Mature α–Factor" Cell, vol. 30 (1982) pp. 933–943.
Boizet, et al., "Isolation and structural analysis of the phospho–β–galactosidase gene Streptococcus lactis Z268" Gene, vol. 62 (1988) pp. 249–261.
Maerina, et al. "A cloning vector able to replicate in Escherichia coli and Streptococcus sanguis" Gene. vol. 19 (1982) pp. 345–353.
Wobler, et al., "Bacterial ice–nucleation proteins" TIBS, vol. 14, (1989) p. 179.
Arai, et al., "Freeze Texturing of Food Materials by Ice––nucleation with the Bacterium Erwinia ananas." Agric. Biol. Chem., 50(1), pp. 169–175 (1986).
Vali, "Quantitative Evaluation of Experimental Results on the Heterogeneous Freezing Nucleation of Supercooled Liquids" J. of Atmos. Sci., vol. 28 (1971) pp. 402–409.
Yanisch–Perron, et al "Improved M13 phage cloning vectors and host strains: nucleotide sequences of the M13mp18 and pUC19 vectors" Gene, 33 (1985) pp. 103–119.
Fleig, et al. "Construction of LYS2 cartridges for use in

*Primary Examiner*—Mary E. Mosher
*Attorney, Agent, or Firm*—Vogt & O'Donnell

[57] ABSTRACT

Ice nucleation is promoted in an ingestible biological material by treating the material with an ice-nucleating protein carried by a yeast or lactococcal GRAS microorganism, or a fraction thereof, transformed by a plasmid vector carrying a gene coding for the ice-nucleating protein.

2 Claims, 21 Drawing Sheets

OTHER PUBLICATIONS genetic manipulsation of *Saccharomyces cerevisiae*" *Gene, 46 (1986) pp. 237–245*.

Pridmore, "New and versatile cloning vectors with kanamycin–resistance marker" Gene, 56 (1987) 309–312.

Holland et al. "The Primary Structure of a Glyceraldehyde–3–phosphate Dehydrogenase Gene from *Saccharomyces cerevisiae*" J. of Biol. Chem 264:19 (1979) pp. 9839–9845.

Alton, et al. "Nucleotide sequence analysis of the chloramphenicol resistance transposon Tn9", Nature, vol. 282 (1979) pp. 864–869.

Ozkaynak, et al. "The yeast uloiquitin genes: a family of natural gene fusions" The EMBO Journal, vol. 6 No. 5 pp. 1429–1439 (1987).

Valls, et al. "Protein Sorting in Yeast: The Localization Determinant of Yeast Vacuolar Carboxypeptidase Y Resides in the Propeptide" Cell, vol. 48 (1987) pp. 887–897.

Chen, et al. "Construction and properties of a new insertion vector, pJDC9, that is protected by transcriptional terminators and useful for cloning of DNA from *Streptococcus pneumoniae*" *Gene, 64 (1988) pp. 155–164*.

Maki, et al. Ice Nucleation by *Pseudomonas syringae*, Applied Microbiology, 28:456–459, Sep. 1974.

Lindow, Methods of Preventing Frost Injury Caused by Epiphytic Ice–Nucleation–Active Bacteria. Plant Disease vol. 67, No. 3, 327–333, Mar. 1983.

Lindow, et al. Competitive exclusion of BCE+ *Pseudomonas syringae* Strains on leap surface by ICE+ Deletion Mutants of *P. syringae* constructed in vitro. Plant Phytopathology vol. 76, No. 10, p. 1069 (1986).

Lindow, et al. Biological Control of Frost Injury: An Insolate of *Erwinia herbicola* Antagonistic to Ice nucleation Active Bacteria, Phytopathology vol. 73 No. 8, (1983) pp. 1097–1106.

Kozloff, et al. Ice Nucleating Activity of *Pseudomonas syringae* and *Erwinia herbicola*, J. Bacteriology vol. 153 No. 1, pp. 222–231 Jan. 1983.

Phelps, Release of Cell–Free Ice Nuclei by *Erwinia herbicola*. J. Bacteriology vol. 167, No. 2, pp. 496–502.

Corotto, et al. Ice nucleation activity of *Pseudomonas fluorescens*: mutagenesis, complementation analysis and identification of a gene product, EMBO Journal vol. 5 pp. 231–236.

Derie, et al. Taxonomy of Six Pathovars of *Xanthomonas campestris* Based on SDS–page of Membrane Proteins. Phytopathology vol. 76, No. 10 p. 1117.

Paulin, et al. Ice nucleation activity among *Phytopathogenic bacteria*. Proc. Int. Conf Plant Path Bact. Angers. vol. 2, pp. 725–731 (1978).

Anderson, et al. The Effects of Streptomycin, Desiccation, and UV Radiation on Ice Nucleation of *Pseudomonas viridiflava*. Plant Physiol. vol. 80, pp. 956–960 (1986).

Kozloff, et al. Phosphatidylinositol as a Component of the Ice Nucleating Site of *Pseudomonas syringae* and *Erwinia herbicola*. Science vol. 226 pp. 845–846 (1984).

Wobler, et al. Identification and Purification of a bacterial ice–nucleation protein. Proc. Natl. Acad. Sci. vol. 83, pp. 7256–7260, Oct. 1983.

Wobler, et al. Structural Modeling of the Ice Nucleation protein of *Pseudomonas syringae*. Biophysical Journal vol. 49, 293a. (1986).

Makino, Micropeptide Method, A New Technique for Detecting Ice–Nucleation Activity of Bacteria and It's Application. Ann. Phytopath. Soc. Japan 48(4) pp. 452–457 Sep. 1982.

Duman, et al. The role of Hemolymph proteins in the Cold Tolerance of Insects. Ann. Rev. Physiol. vol. 45, pp. 261–270 (1983).

Fall, et al. Association of an ice–nucleating pseudomonad with cultures of the marine dinoflagellate, *Heteroscapsa niei*. Journal of Marine Research vol. 43 pp. 257–265 1985.

Lindow et al., Proc. Am. Phytopathol. Soc. (1977) 4:169.

Arny et al., Nature (1976) 262:282–284.

Lindow et al., Phytopathology (1978) 68:523–527.

Lindow et al., Proc. Am. Phytopathol. Soc. (1977) 3:224.

Lindow et al.: Applied and Environmental Microbiology 36, 831 (1978).

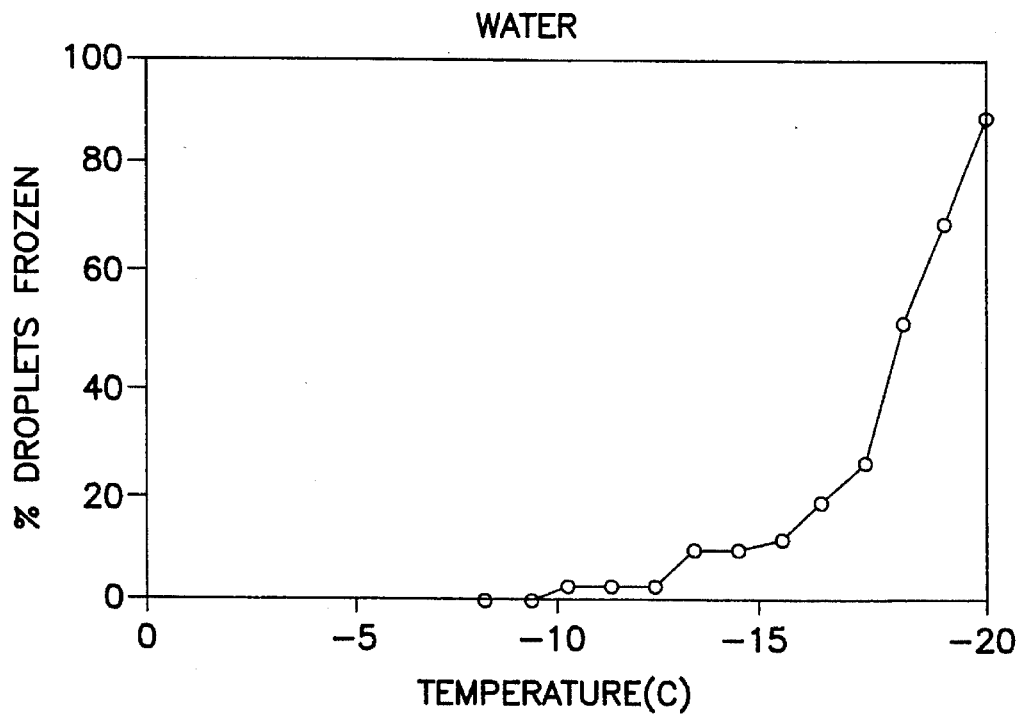
FIG. IA
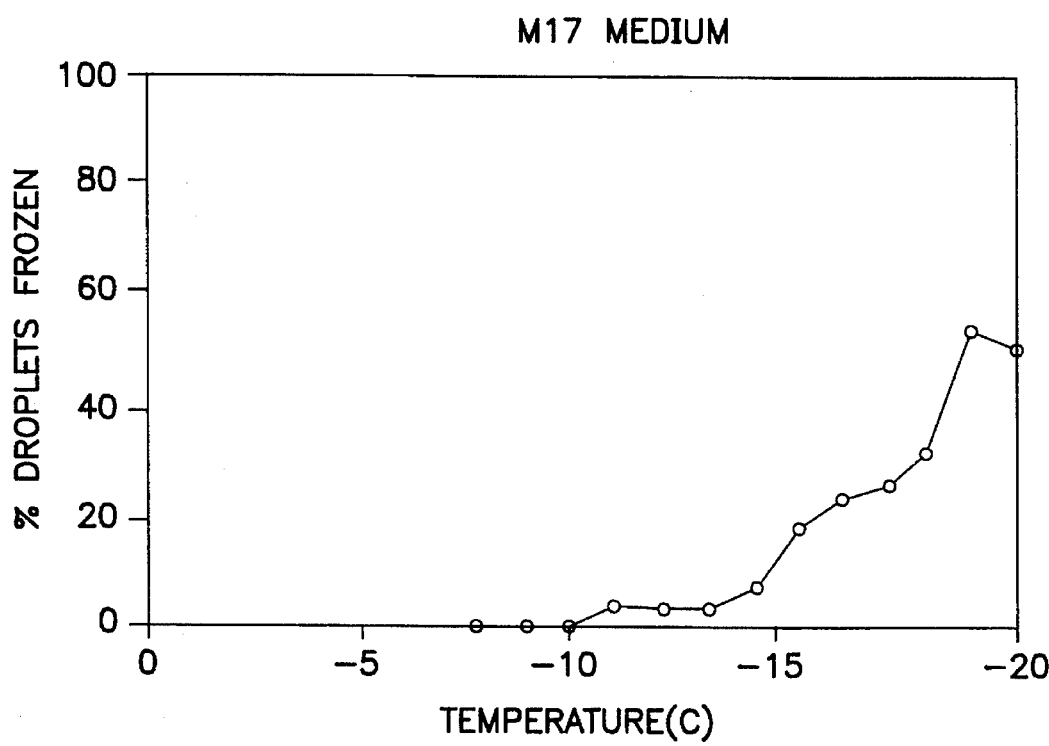
FIG. IB

YP42 + pDP114

YP42 + pDP115

PLASMID VECTORS AND GRAS MICROORGANISMS PROMOTING ICE NUCLEATION

CROSS REFERENCE TO RELATED APPLICATION

This application is a continuing appplication of Application Ser. No. 07/596,203, filed Oct. 11, 1990, now abandoned.

BACKGROUND OF THE INVENTION

This invention relates to the nucleation of ice in the freezing of foodstuffs and like biological materials and additives for use in promoting such nucleation.

It is important in the freezing of foodstuffs and like biological materials to minimize the formation of large ice crystals since this has a generally deleterious effect on the texture or condition of the material after thawing. It is found that if freezing is effected in the presence of a large number of nuclei promoting ice formation, all the water present can be frozen in the form of small crystals. However, there are serious limitations on the substances which can be added to food, so that nucleating additives have not hitherto been used to a significant extent.

It has recently been proposed to add to foodstuffs cells of *Pseudomonas syringiae* which carry a native protein capable of ice nucleation. This organism is widely distributed and is responsible in many substances for premature freezing of growing plants such as grape vines, strawberry, potato, tomato plants and the like. It is found that cells of *P. syringiae* can promote ice nucleation and the formation of small ice crystals when present in foodstuffs during freezing. In addition, U.S. Pat. No. 4,200,228 describes a method using such organisms in snow making while International Patent Application WO 83/03831 describes the transformation of certain host microorganisms with DNA coding for the ice nucleation protein in order to produce microbial agents of use in inhibiting supercooling.

However, although yeasts and other fungi have been considered as possible hosts in the above methods, only *E. coli* and the native organisms such as *P. syringiae* are specifically mentioned. There is thus no specific mention of any host microorganisms which could be used practically as additives to biological materials for ingestion such as foods.

*P. syringiae* is a member of the genus Pseudomonas. Certain species of the genus are pathogens, for example the human pathogen *P. aeruginosa*. Some strains of *P. syringiae* are also known to be pathogens for certain plants. Similarly, certain strains of *E. coli* are well known human pathogens. Consequently, they would not be practicable for use in food additives. Even when used in the form of killed cells, there is always the danger of incomplete killing and subsequent proliferation of surviving organisms on storage and thawing of the foodstuff and such microorganisms are not included in the lists of organisms designated GRAS (Generally Regarded as Safe) in the U.S. Code of Federal Regulations, Vol. 21, Parts 170 to 199, April 1986, published by the U.S. Government Printing Office.

SUMMARY OF THE INVENTION

The present invention is based on the concept of isolation of the gene responsible for expression of an ice-nucleating protein in *P. syringiae* and other organisms and using this in an appropriate vector to transform organisms which are listed as GRAS whether in live or killed form, in relation to foodstuffs, as additives to foodstuffs or other ingestible biological materials.

According to one aspect of the present invention we provide additives for promoting ice nucleation in ingestible biological materials at sub-zero temperatures comprising a protein capable of promoting said ice nucleation carried by GRAS microorganisms transformed by a vector carrying one or more genes coding for expression of said protein or by fractions of said microorganisms.

According to a further aspect of the invention we provide ingestible biological materials carrying one or more of said additives according to the invention.

Foodstuffs which may advantageously be treated in accordance with the invention include vegetables, fruits, fish, meats, prepared frozen dishes, ice cream, frozen doughs, frozen juices and freeze dried foodstuffs. Pharmaceutical products of interest include freeze dried materials and blood fractions such as cryoprecipitate.

According to a further aspect of the invention, we provide a method of promoting ice-nucleation in ingestible biological materials wherein the materials are treated with one or more additives according to the invention.

According to a further aspect of the invention, we provide a method of freezing ingestible biological materials wherein the materials are treated with one or more additives according to the invention and the temperature thereof lowered to effect freezing. Such temperatures are conveniently within the range $-5°$ to $-20°$ C.

BRIEF DESCRIPTION OF THE DRAWINGS

FIG. 1A illustrates the results of a qualitative drop freeze assay for water.

FIG. 1B illustrates the results of a qualitative drop freeze assay for M17 medium.

DETAILED DESCRIPTION OF THE INVENTION

Figure 1C:
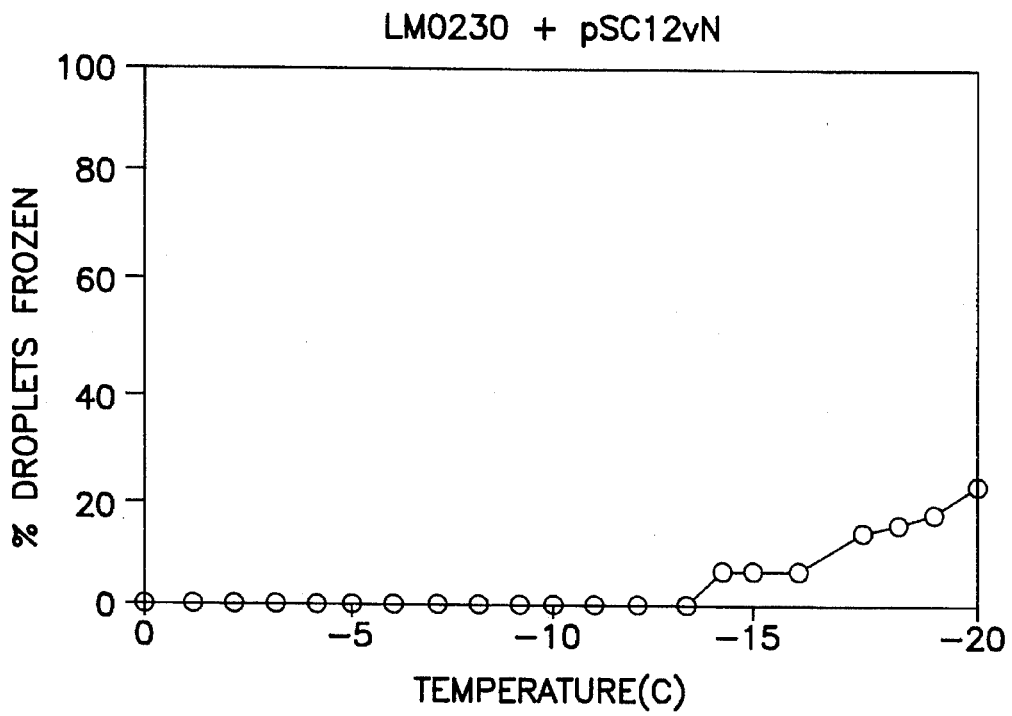
FIG. 1C illustrates the results of a qualitative drop freeze assay for M17 medium plus LM0230 with pSC12vN.

The term GRAS as used herein has the meaning given in the above U.S. Federal Regulations. Such microorganisms include yeasts, e.g. *Saccharomyces cerevisiae* or carlsbergensis, lactic acid bacteria, e.g. *Lactococcus lactis, Lactobacillus bulgaricus* etc., vinegar bacteria and certain filamentous fungi, e.g. Aspergillus species.

The microorganisms may be used as whole cells or as fractions thereof. There is evidence to show that whole cells are effective even when the ice-nucleating protein is retained within the cell. In some instances, however, it may be advantageous to fragment the cells and to use only fractions carrying the active protein, for example cell wall fragments.

The microorganisms will be transformed by a vector appropriate for the purpose. In general, plasmids will be used when transforming prokaryotic hosts such as bacteria. Yeasts may be transformed with plasmids which may, however, be designed to integrate the active gene into the chromosomal DNA.

The DNA coding for the ice nucleating protein may be obtained from naturally occurring organisms such as *P. syringiae, P. fluorescens, P. coronafasciens, Xanthomonas translucens* or *Erwinia herbicola*. Alternatively, the DNA may be synthesized on the basis of genes which have already been sequenced e.g. INAZ (R. L. Green and G. J. Warren, Nature, Vol. 317, 1985, pp 645–648) and INAZ (G. J. Warren et al., Nucleic Acids Research, Vol 14, No. 20, 1986, pp 8047–8060) or the gene sequences described herein.

The isolated gene may be provided with suitable terminal restriction sites enabling it to be inserted into a vector appropriate to the intended host.

Thus, where the intended host is a yeast, e.g. YP42, a suitable plasmid vector is pDP34 (European Patent No. 89810297.5-) usefully modified e.g. the plasmid comprising the *E. coli* vector pUC19, the complete yeast 2 micron plasmid and two yeast selectable auxotrophic markers, e.g. the URA3 gene for easy transformation and low copy number selection of the plasmid in yeast and the dLEU2 allele of the LEU2 gene for induced high copy number.

It should be noted that one should ensure that the initiator codon is the first ATG of the gene since yeast always uses the first ATG it finds to initiate translation and if necessary any ATGs 5' of the "real" ATG must be excised.

The plasmids may then be used to transform a suitable yeast strain and selected for the presence of the auxotrophic markers.

We have found that yeast strains transformed as described above do not always produce the ice nucleating protein in an accessible form and that it is desirable to include a yeast signal sequence to target the protein to the cell surface. Such a sequence may be, for example, the PH05 signal sequence (W. Bajwa et al., Nucleic Acids Research, Vol 12, No. 20, 1984, pp 7721–7739) or the alpha factor pre-pro leader sequence (J. Kurjan and I. Herskowitz, Cell 30, 1982, pp 933–943). We have further found that when the alpha factor leader sequence is used, a linker sequence is preferably present between the pre-pro peptide sequence and the gene of interest, e.g. the 8 amino acid linker in native alpha factor.

It is also possible to target the ice nucleation protein to a specific organelle within the cell, e.g. the vacuole. For this purpose, the pre-pro sequence of carboxypeptidase Y (CPY) may be introduced since this protein is known to be directed to the vacuole.

*Lactococcus lactis* is a particularly safe and acceptable food grade microorganism e.g. strain LM0230. One suitable plasmid for use in transforming this organism is pSC12vN which consists of the *E. coli* vector pUG18, the non-inducible erythromycin resistance gene from plasmid pVA838 (reference 2 see below, please) and a *L. lactis* plasmid origin of replication. However, this requires incorporation of a promoter in addition to the gene of interest, and we have found the modified tacII promoter to be particularly useful. A more direct approach to expression in *L. lactis* is to use the promoter of an *L. lactis* gene such as the phospho-β-galactosidase gene of strain Z268 (reference 1).
(B. Boizet et al., Gene 62, 1988, 249–261)
(F. L. Macrina et al., Gene 19, 1982, 345–353)

The following microorganisms have been deposited at the National Culture of Industrial and Marine Organisms, Aberdeen, Scotland on 24 Oct. 1989 under the accession numbers stated below.

| S. cerevisiae | YP42 | NCIMB 40215 |
| L. lactis | LM0230 | NCIMB 40216 |
| E. coli | BZ234(pUC21ENA3) | NCIMB 40217 |

The above *E. coli* NCIMB 40217 has been transformed with plasmid pUC21ENA3 referred to hereinafter.

The plasmid pDP143 was deposited pursuant to the Budapest Treaty on Nov. 10, 1994, in the Collection Nationale de Cultures de Microorganismes (CNCM), Institut Pasteur, 28 rue du Dr. Roux, F-75724 Paris Cedex 15, France, where it was given the number CNCM I-1490.

EXAMPLES

Example 1

Isolation of ice nucleating Pseudomonads

A sample of about 15 gms of leaves and flowers were taken from the plants in the woods next to the Nestlé Research Centre, Vers-chez-les-Blanc and placed in a sterile 500 ml shake flask. 100 ml of sterile peptone (0.1%), phosphate (50mM, pH 7) buffer was added and the flask shaken at 300 rpm at 30° C. for 1 hr. The liquid was taken off and the cell debris and bacteria pelleted out by centrifugation at 10,000 rpm for 5 mins. The supernatant was discarded and the pellet resuspended in 10 ml of peptone/phosphate buffer. From this 5 aliquots of 0.04 ml were plated onto Kings agar plates supplemented with 40 µg/ml cycloheximide and 0.1% cetrimide and incubated at room temperature for 48 hrs. The plates are important and are fairly Pseudomonas specific (the cycloheximide destroys fungi or their germinating spores and the cetrimide is a biological detergent that kills most bacteria except pseudomonads).

The plates contained two basic types of colonies. The first being small and forming a background of individual colonies, while superimposed on this were the second larger colonies, (thus making it impossible to say that a large colony was not contaminated with a small).

Two of the plates were tested for the general presence of Ice Nucleation Activity (INA) by washing the cells off of the plates in 5 ml of peptone/phosphate buffer and testing them in the drop freeze assay. This requires a boat in aluminum coated with paraffin, (achieved by washing a 1% solution of paraffin wax (solid) in xylene onto the surface of the aluminum and allowing the xylene to evaporate). 10 µl drops of the plate washings were placed on the aluminum boat along with controls at −9° C. and freezing scored. Both plate washings froze reproducibly under these conditions within 30 seconds while the controls would freeze only occasionally if at all. This test was repeated at the more critical −5° C. temperature where the plate washings again froze quickly and reproducibly, while the controls were never seen to freeze at this temperature. This confirmed the presence of INA bacteria in these isolates.

From the remaining plates 300 individual colonies were picked with sterile tooth picks into microtitre plates and grown at room temperature for 3 days. 10 µl droplets were then transferred with a multi-channel pipette onto a paraffin coated aluminum boat and placed at −5° C. From this were identified 10 INA bacteria, one with weak activity. Two of these, INA5 and INA7, were purified to pure cultures as determined by plating out the cells to single colonies and taking 50 random clones and testing for ice nucleating activity at −5° C.

Figure 1D:
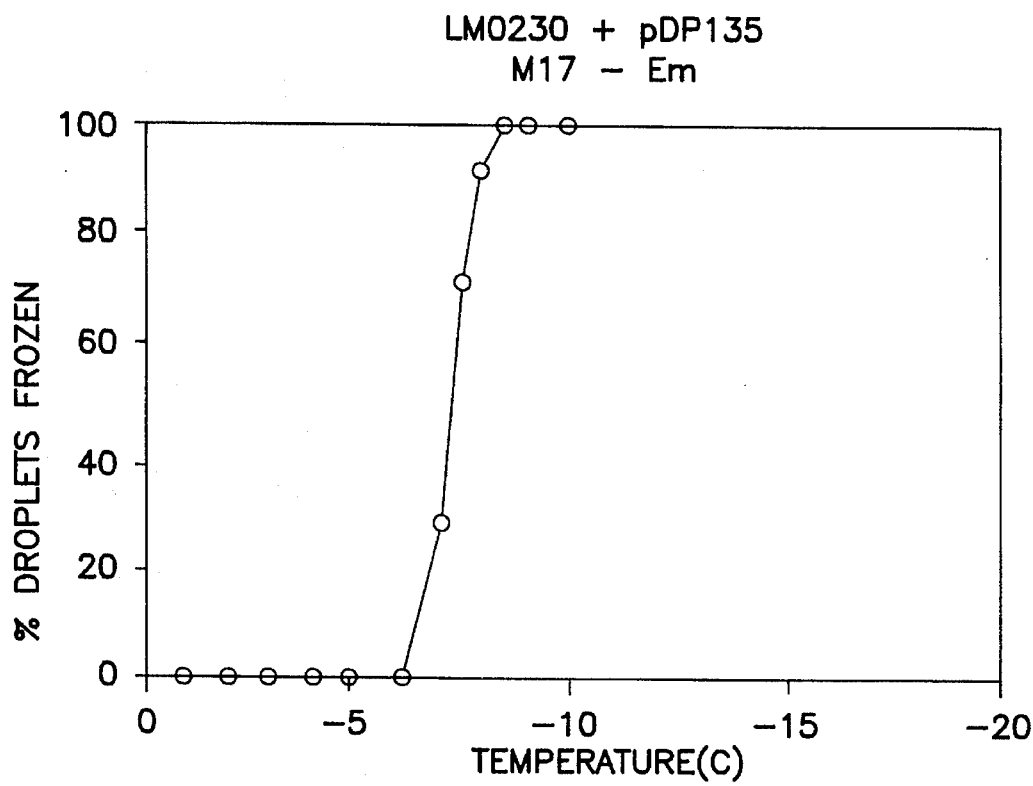
FIG. 1D illustrates the results of a qualitative drop freeze assay for M17 medium plus LMO230 with pDP135.

Standard Qualitative Drop Freeze Assay 50 droplets of 10 µl volume are arranged on a paraffin coated aluminum boat and placed onto the surface of an alcohol bath at a preselected temperature. The boat is timed for 1 min and the number of frozen droplets recorded. This is expressed as the percentage of droplets frozen at that temperature. A comparison of the results obtains with water (A), M17 medium (B), M17 medium plus LM0230 with plasmid pSC12vN (C) and M17 medium plus LM0230 with plasmid pDP135 (D) is illustrated in FIG. 1 wherein the percentage droplets frozen is plotted as ordinate against temperature (−°C.) as abscissa.

Standard Quantitative Drop Freeze Assay

This is based on the calculations of G. Vali (J.Atmos.Sci. 28,1971, 402–409) for the quantification of ice nucleating substances. A standard assay involves taking 1 ml of culture and pelleting the cells by centrifugation for 2 mins. The culture medium is discarded and the cells resuspended in 1 ml of TE (10 mM Tris, 1 mM EDTA pH 7.0). Serial dilutions are prepared to $10^{-7}$ from this suspension in TE. 10 droplets from each dilution are pipetted onto a paraffin coated aluminum boat and the boat then placed on an alcohol water bath at a preselected subzero temperature. After 3 mins, the number of frozen droplets and their position in the dilution series is recorded. The number of ice nuclei at that temperature is calculated according to Vali's equation;

$$N(t) = \ln \frac{1}{(1-f)} \times \frac{10^D}{V}$$

where N(t) is the number of ice nuclei at that given temperature; f is the fraction of frozen droplets; D is the number of dilutions in the series; and V is the volume of the droplet in ml. This is then normalized for the cell concentration and finally expressed as the log of this number. This is a quantitative calculation for an ice nucleating substance and is based on the ordered freezing in the dilution series, ie, as the temperature drops, firstly the undiluted droplets freeze, followed by the $10^{-1}$ dilution series and so on. This can not be easily used to quantify the freezing of pure water, which is essentially a random process. Hence the use of the qualitative assay for these non-ice nucleating solutions.

Isolation of chromosomal DNA 100 ml of Kings medium was inoculated with INA5 and INA7 and grown at 30° C. overnight. The cells were centrifuged at 10,000 rpm for 5 mins and the supernatant discarded. The cells were resuspended in 5 ml of 50 mM Tris, 50 mM EDTA pH 8.0, 0.5 ml of a 10 mg/ml fresh solution of lysozyme in 250 mM Tris, pH 8.0 added and incubated on ice for 45 mins. To this was added 1 ml of STEP (0.5% SDS, 50 mM Tris, pH 7.5, 0.4 M EDTA and 1 mg/ml proteinase K) and incubated at 60° C. for 3 hrs. This was extracted twice with 7 ml of 1:1 phenol/chloroform mix and the phases separated by centrifugation. 15 ml of ethanol were added to precipitate the DNA and the liquid was carefully poured off. The DNA was dissolved in 5 ml of 10 mM Tris pH 8.0, 10 mM EDTA, 0.1 mg/ml RNase with incubation at 60° C. for 2–3 hrs (this is joint solubilization and RNase treatment). The DNA was again precipitated with 10 ml ethanol and the DNA was spooled out (the mass of DNA was removed by twisting it around a toothpick against the side of the tube). This DNA was the dissolved in 5 ml 10 mM Tris pH 7.5, 0.1 mM EDTA giving a solution of about 1 mg/ml.

Cloning of the INA gene

Oligo 17 is a mixed oligonucleotide based on an 8 amino acid motif of the repeated sequence that is conserved in both INAZ and INAW [of *P. syringiae* (R. L. Green & G. J. Warren, Nature Vol 317, 1985, pp 645– 648) and *P. fluorescens* (G. J. Warren et al, Nucleic Acids Research, Vol 14, no 20, 1986, pp 8047–8060) respectively] and repeated almost 30 times in each case (below).

| A | G | Y | G | S | T | Q | T | |
|---|---|---|---|---|---|---|---|---|
| Ala | Gly | Tyr | Gly | Ser | Thr | Gln | Thr | [SEQ ID NO:23] |
| T | T | T | T | T | T |   | A | 23 mer, |
| 5'GCC | GGC | TAC | GGC | AGC | ACC | CAG | AC3' | [SEQ ID NO:1] |
| G |   | G |   | G |   | G |   | 1024 mix |
| A |   | A |   | A |   | A |   | |

Analytical restriction digests were carried out on both INA5 and INA7 DNA's and the fragments separated by agarose gel electrophoresis. This was then transferred onto Zetaprobe nylon membrane and hybridized with radioactively kinased Oligo 17 (T. Maniatis et al., Molecular Cloning. A Laboratory Manual, Cold Spring Harbor, N.Y., 1982). After washing, the filter was autoradiographed at −70° C. with an intensifying screen for 6 hrs. The autoradiograph showed some background, nonspecific hybridization, but also good signals. Firstly, both INA5 and INA7 are identical. Fragment sizes were as follows (INAZ in brackets); SacI 7 kb (?), SacI+ BglII 6 kb (3.4 kb), BglII 16–19 kb (very large!), BglII+ EcoRI 5 kb (5 kb), EcoRI 9 kb (23 kb), EcoRI+ PvuI 7 kb (3.75 kb), PvuI 8 kb (?), and SalI 1 kb (1 kb). Therefore, although the EcoRI+ BglII and the SalI fragments are the same, most of the other restriction digests are different.

It was decided to clone the 5 kb BglII+ EcoRI fragment into a pUC vector, and screen with Oligo 17. 60 µg of INA5 DNA was digested with the restriction enzymes BglII and EcoRI and the fragments separated on a 0.7% agarose gel. The area of gel containing fragment sizes 4.4– 5.5 kb was cut out of the gel and electroeluted. This mixture was cloned into the plasmid pUG21 [a pUG19 (C. Yanisch-Perron et al, Gene 33, 1985, pp 103 119) based plasmid with an alternative cloning array created with synthetic oligonucleotides being cloned into BamHI—SacI digested pUC19] as follows (The mature amino acid sequence of the LacZ gene is shown on the upper line; the DNA sequence and it's complement are shown in the middle two lines; the restriction enzyme recognition sites are shown in the lower line. The synthetic oligonucleotides are shown in capital letters.):

Discard supernatant and resuspend in $1/10^{th}$ of original volume of 50 mM CaCl; 20% glycerol.

These E. coli cells are now competent and may be used immediately or they may be frozen at −70° C. for future use.

Transformation

A 100 µl aliquot of competent cells is placed in a pre-chilled sterile glass tube, The above ligation reaction is added to this and mixed well, Incubate on ice for 20 mins, Heat for 2 mins at 42° C., These cells may now be plated directly onto the selective plates (as in the case of ampicillin selection) or add 500 µl of YT medium and incubate at 37° C. for 2 hrs (as in the case of kanamycin and erythromycin selection).

From these selective transformation plates 8 microtitre plates of colonies (768) were picked. These were replicated onto Zetaprobe nylon filter laid on a YT agar plate supplemented with Ampicillin and grown at 37° C. overnight. The colonies were lysed directly on the filters and hybridized with radioactively kinased Oligo 17. After washing, the filters were autoradiographed at room temperature for 45 mins to identify 10 hybridizing clones;

| | Thr | Met | Ile | Thr | Pro | Ser | Leu | His | Ala | Cys | Arg | Ser | Thr | Leu | Glu | Asp | Pro | |
|---|---|---|---|---|---|---|---|---|---|---|---|---|---|---|---|---|---|---|
| $5'$atg | acc | atg | att | acg | cca | agc | ttg | cat | gcc | tgc | agg | tgc | act | cta | gag | GAT | CCA | |
| $3'$tac | tgg | tac | taa | tgc | ggt | tcg | aac | gta | cgg | acg | tcc | acg | tga | gat | ctc | cta | gGT | |
| | | | | | | < Hind3 >< | | SphI >< | | PstI >< | | SalI >< | | XbaI >< | | BamHI >< | |

| Arg | Val | Pro | Ala | Leu | Ala | Asp | Leu | Ser | Arg | Ser | Ser | Asn | Ser | Leu | [SEQ ID NO: 3] |
|---|---|---|---|---|---|---|---|---|---|---|---|---|---|---|---|
| CGC | GTG | CCG | GCG | CTA | GCA | GAT | CTC | TCG | AGG | AGC | Tcg | aat | tca | ctg$^{3'}$ | [SEQ ID NO: 2] |
| GCG | CAC | GGC | CGC | GAT | CGT | CTA | GAG | AGC | TCC | tcg | agc | tta | agt | gac$_{5'}$ | [SEQ ID NO: 4] |
| MluI | >< | NaeI | >< | NheI | >< | BglII | >< | XhoI | >< | SacI | >< | EcoRI> | | | |

Example ligation 0.4 pmole (1 µl) of BglII—EcoRI digested pUC21, 1.5 pmole (3 µl) of purified BglII—EcoRI INA5 fragment, 13 µl of TE buffer, Mix well in a microfuge tube, then heat at 56° C. for 2 mins, Add 2 µl of 10× T4 DNA ligase buffer, [660 mM Tris pH 7.5;

50 mM MgCl; 50 mM dithiothreitol (DTT); 10 mM adenosine-5'-triphosphate (ATP); 200 µg/ml bovine serum albumin (BSA)], Add 1 µl= 1 unit of T4 DNA ligase, Mix well and incubate at 4° C. for 3–4 hrs.

Example E. coli competent cells

Inoculate 100 ml of YT medium (8 gm/l Bacto tryprone; 5 gm/l Bacto Yeast extract; 5 gm/l NaCl), with 1 ml of fresh overnight culture of BZ234 cells, Incubate culture at 37° C. until $OD_{600}=0.4$, Pellet cells in a centrifuge at 10,000 rpm for 5 mins, Discard supernatant and resuspend pellet in an equal volume of sterile 50 mM CaCl at 4° C., Incubate on ice for 20 mins, Pellet cells at 10,000 rpm for 5 mins, ENA = E. coli ice Nucleating Activity.

| Plate | Position | ENA |
|---|---|---|
| 1 | F1 | 1 |
| 1 | F2 | 2 |
| 3 | H9 | 3 |
| 5 | D5 | 4 |
| 5 | F6 | 5 |
| 6 | A3 | 6 |
| 6 | C8 | 7 |
| 7 | C6 | 8 |
| 7 | E10 | 9 |
| 8 | B1 | 10 |

Figure 2A:
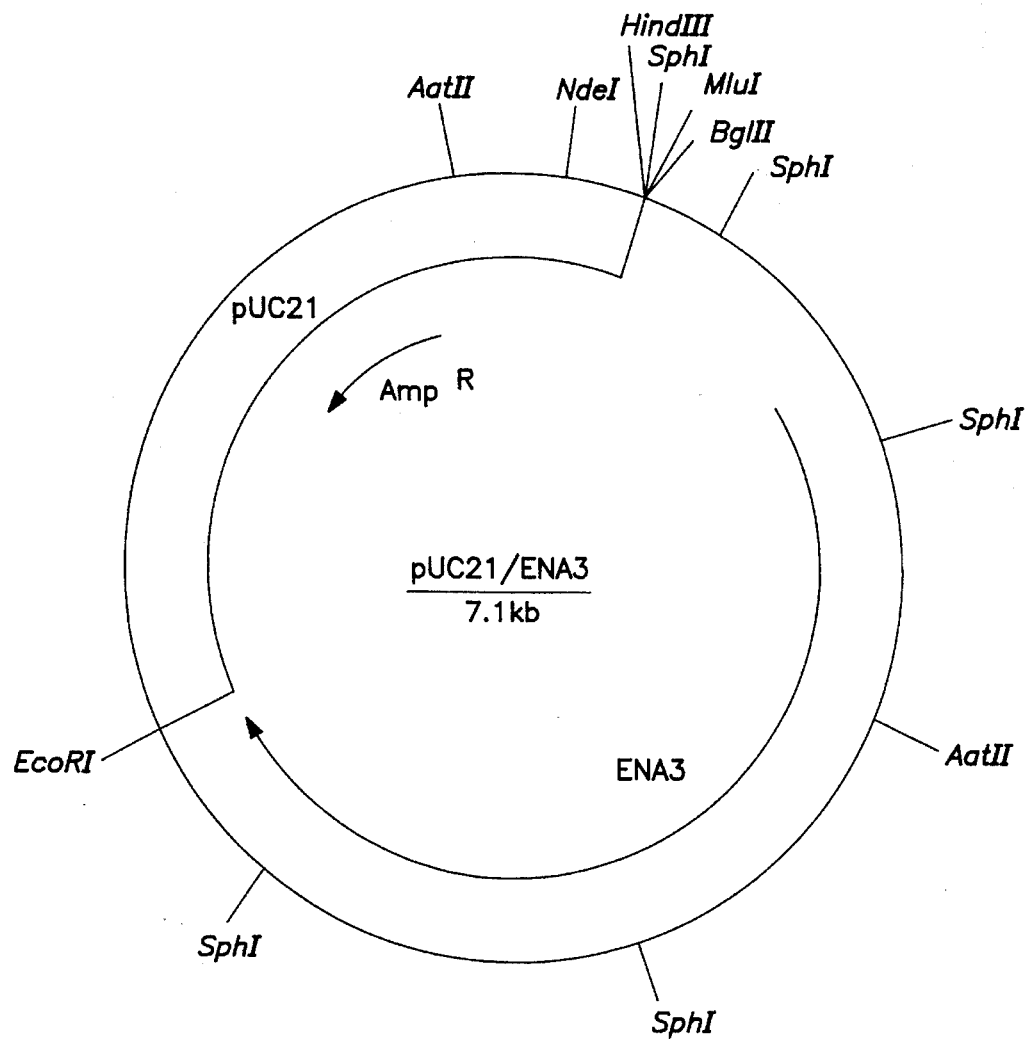
FIG. 2A is a map of the plasmid pUC21/ENA3.
Figure 2B:
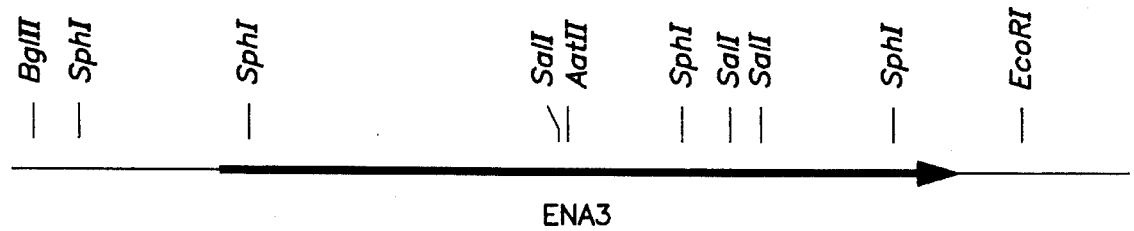
FIG. 2B is a restriction map of the ENA3 gene.

All of these colonies were shown to freeze at −5° C., usually within 20–30 seconds, whereas the controls did not freeze after 10 mins. Small scale DNA preparations were made from all 10 clones and the DNA digested with EcoRI and BglII (the enzymes used to clone the gene and which should release a unique 4.5 kb insert and the 2.7 kb plasmid vector). ENA 4 and 10 showed the presence of two insert bands and were therefore put aside. Analytical digestions showed ENA 1 and 6 contained mixtures of plasmids. From these data ENA3 was chosen for further analysis. The plasmid pUC21/ENA3 is shown diagrammatically in FIG. 2A of the accompanying drawings; FIG. 2B shows a restriction map of the ENA3 gene.

An extensive restriction map of the plasmid ENA3 was constructed as a starting point. This showed there to be considerable but not prefect homology between the ENA3 insert and the published INAZ gene from Pseudomonas syringiae. The restriction map was used for the extensive subcloning of the ENA3 insert and subsequent DNA sequence analysis of these subclones.

The complete BglII—EcoRI fragment has been sequenced and contains 4446 bp, namely 12 base pairs shorter than the published INAZ gene. There are two minor insertions/deletions of 1 nucleotide, both outside the protein coding sequence. These are the insertion of a G at bp 594 in the ENA3 gene and the deletion of a nucleotide at bp 4396. A more important deletion occurs around bp 1168–1179 with the deletion of 12 base pairs which preserves the protein reading frame (a 4 amino acid deletion). This occurs at a 4× repeated sequence motif of 'AACGCC'. Most probably these repeats are responsible for the deletion.

The two P.syringie sequences show an overall homology of about 93% (determined by the Bestfit program of UWGCG) at the DNA level with the majority being the usual T→C and G→A changes. At the protein level the homology rises to about 98%. The changes being the 4 amino acid deletion plus 37 amino acid substitutions, only 13 of which are 'conservative'

Example 2

Expression of ENA3 in yeast

An important first step for the expression of the ENA3 ice nucleating gene in yeast is the removal of the two 'ATG's that lie immediately (14 bp and 8 bp) 5' of the real 'ATG'. This is required as yeast always takes the first 'ATG' that it finds after mRNA initiation, which in this case would result in a peptide of 4 amino acids in length, thus very little of the ice nucleation protein. A second consideration is the addition of a useful restriction site to aid the addition of yeast promoters and/or signal sequences.

Construction of ENA3-term

Figure 3A:
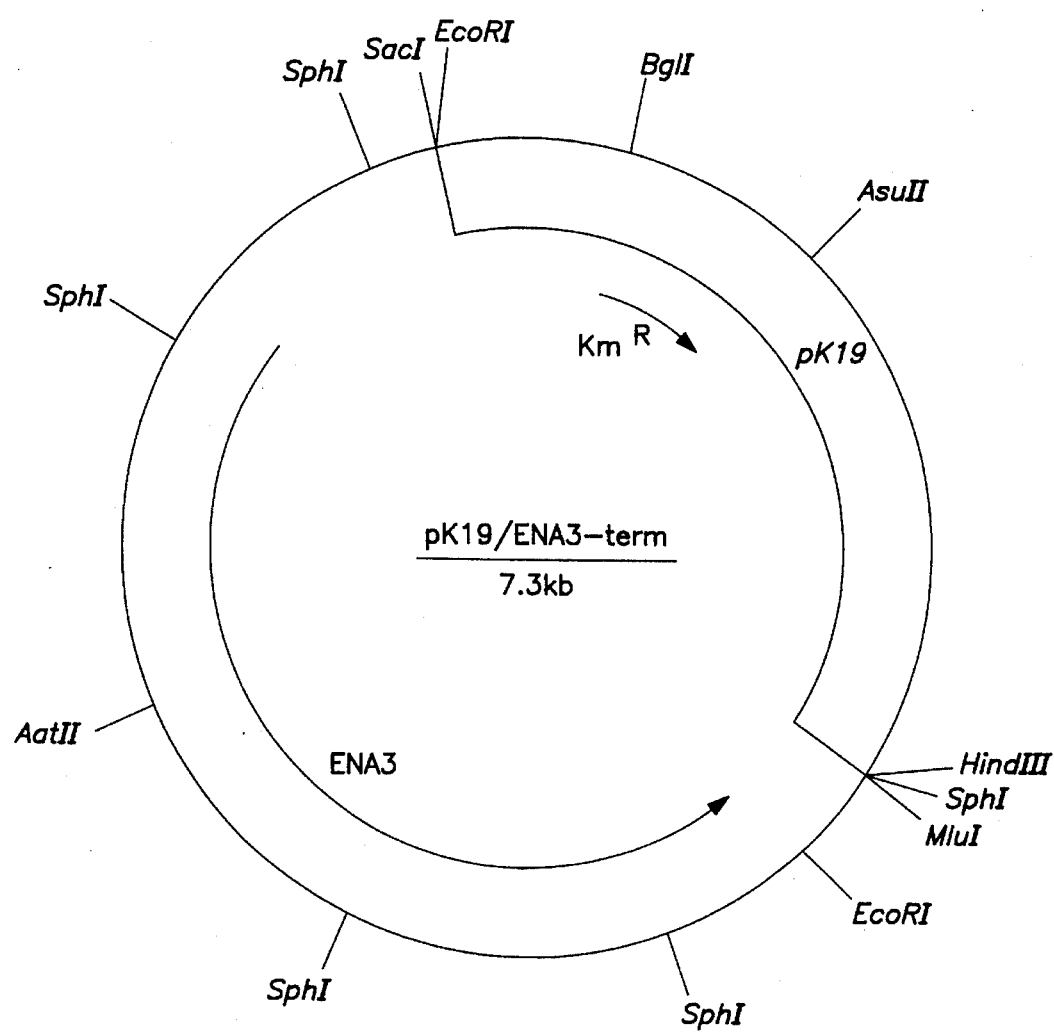
FIG. 3A is a map of the plasmid pK19/ENA3-term
Figure 3B:
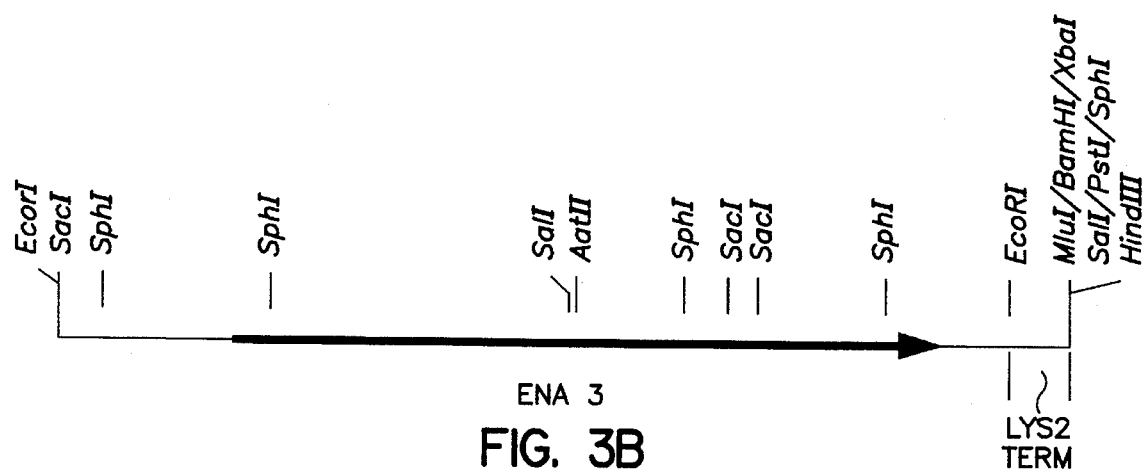
FIG. 3B is a restriction map of ENA3-term.

Plasmid ENA3 was digested with the restriction enzyme EcoRI and the 5' overhang filled in with Klenow enzyme. This was subsequently digested with BglII and PvuI and then the DNA fragments resolved on an agarose gel. The 4.5 kb fragment was cut out and electroeluted. Plasmid pUC21/LYS2-term2 (R. D. Pridmore unpublished results) is the E. coli vector pUC21 containing the yeast LYS2 bi-directional terminator (U. N. Fleig et al., Gene 46,1986, pp 237–245). This plasmid was digested with NheI and the 5' overhang Klenow repaired (Maniatis et al.). This was subsequently PstI digested and the fragments separated on a 2% agarose gel. The 190 bp fragment was cut out and electroeluted. These two fragments were mixed with PstI and BamHI digested pK19 (R. D. Pridmore, Gene 56, 1987, pp 309–312) vector and ligated. Transformants were initially tested for ice nucleation activity. One of these was then further characterized by restriction enzyme analysis to confirm plasmid pK19/ENA3-term which is shown diagrammatically in FIG. 3A of the accompanying drawings. FIG. 3B shows a restriction map of ENA3-term, in which LYS2 T represents the yeast LYS2 bi-directional terminator.

This plasmid was then digested with the restriction enzymes AatII and SacI and the 5 kb fragment gel purified and dephosphorylated (Maniatis et al.). This fragment was prepared to accept the future promoter-ENA3 5' constructions.

Construction of pDP105

The construction of pDP105 involves the isolation of a DNA fragment starting at the TaqI restriction site, about +8 bp from the 'ATG' of the ENA3 gene, to the SphI restriction site, about +185 bp. The DNA sequence of the 'ATG' and the ENA3 gene until the TaqI restriction site is replaced with synthetic oligonucleotides, which also add the new restriction enzymes sites EcoRI and NdeI 5' of the 'ATG'.

Plasmid EC1 is an ENA3 subclone containing a 750 bp SphI fragment covering the promoter and 'ATG'. EC1 was digested with the restriction enzymes SphI and TaqI, the fragments separated on a 2% agarose gel and the 180 bp fragment cut out and electroeluted. This fragment was mixed with the synthetic oligonucleotides 124 and 125 and ligated into SphI and EcoRI digested pUC19 cloning vector. Plasmids bearing the correct insert were identified by restriction analysis and finally confirmed by DNA sequence analysis. This places EcoRI and NdeI restriction 5' and overlapping the 'ATG' respectively. DNA sequence around the 'ATG' of the ENA3 gene showing the TaqI restriction site;

TaqI
———                          175 bp

5'ATGCTGTAATGAATATCGACAAA3'---------------[SEQ ID NO:5]

3'TACGACAT<u>TAC</u>TTATAGCTGTTT5' ---------------SphI [SEQ ID NO:24]

DNA sequence of the oligonucleotides used as linkers;

<NdeI>     TaqI

<EcoRI>    ———

5'AATTCATATGAATAT3'     [SEQ ID NO:6]

3'GTATACTTATAGC5'     [SEQ ID NO:7]

GAPDH promoter addition

Two GAPDH promoter constructions were prepared and tested. The kb HindIII fragment containing the complete GAPDH gene (J. P. Holland & M. J. Holland, The Journal of Biological Chemistry, Vol 254, no 19, 1979, pp 9839 9845) was supplied by Ciba Geigy. The gene was excised with HindIII and transferred into the E. coli vector pK19. Two deletions to shorten the promoter were constructed by digesting the plasmid with SmaI (cutting within the pK19 linker array) and either SnaBI (bp 424) or SspI (bp 646), all enzymes giving compatible blunt ends, all self re-ligated. This gave GAPDH promoter lengths of 600 bp and 400 bp respectively for the plasmids pK19/GAPDH-dSna and pK19/GAPDH-dSsp.

The dSna and dSsp promoters were isolated as follows. The plasmids were digested with the restriction enzyme AsuII and the 5' overhang filled in with Klenow enzyme. This was then digested with SacI and the products separated on a 1% agarose gel. DNA bands of the correct size were cut out and the DNA electroeluted out of the gel fragment.

The pDP105 plasmid was digested with the restriction enzyme EcoRI and the 5' overhang filled in with Klenow enzyme. This was then digested with SphI and the fragments separated on a 2% agarose gel. The correct 200 bp fragment was cut out of the gel and electroeluted.

The pDP105 ENA3 5' DNA fragment was ligated to the two promoters in parallel into the E. coli vector pUC19 digested with SacI and SphI. This gave the plasmids pDP106 (dSsp) and pDP107 (dSna).

Plasmids pDP106 and pDP107 were digested with the restriction enzymes SphI and SacI and the fragments separated on an agarose gel. The 550 bp and 750 bp fragments respectively were cut out of the gel and electroeluted. Plasmid ENA3 was digested with the restriction enzymes AatII and SphI and the fragments separated on an agarose gel. The 1.3 kb fragment was cut out of the gel and electroeluted. This ENA3 5' 1.3 kb AatII—SphI fragment was mixed with the pDP106 and 107 isolated fragments separately and the previously prepared pK19/ENA3-term AatII—SacI 5 kb fragment and ligated. From this was identified the plasmids pDP108 and pDP109 respectively.

GAPDH/CAT promoters

A second line of promoters was constructed that also carried an E. coli promoter between the yeast GAPDH promoter and the ENA3 gene. This was done to facilitate the screening of our constructions for activity before we transformed them into yeast. The E. coli promoter chosen was that of the chloramphenicol resistance gene of Tn9 (N. K. Alton & D. Vapnek, Nature 282, 1979, pp 864–869). Also, to avoid incorporating unwanted E. coli sequences into the construction, the promoter was synthesized and used as a linker between the GAPDH promoter and the ENA3 gene as follows;

|  | AsuII |  | EcoRI NdeI |  |  |
|---|---|---|---|---|---|
| GAPDH | 5'ttCGAATTTTTGAGTTATCGAGATTTTCAGGAGCTAAGGaattcatatg3' |  |  | ENA3 | [SEQ ID NO:8] |
| promoter | 3'aagcTTAAAAACTCAATAGCTCTAAAAGTCCTCGATTCCTTAAgtatac5' |  |  | gene | [SEQ ID NO:9] |

The capital letters denote those that were synthesized, the upper strand being Oligo 141 and the lower Oligo 142. These oligonucleotides were purified as per usual, then dried down and redissolved at a concentration of 300 pico-moles per microliter. 300 pmoles of each oligonucleotide was mixed in a volume of 10 μl of hybridization buffer (150 mM NaCl, 100 mM Tris pH 8.0 and 1 mM EDTA). This was then heated to 95° C. for 5 mins, and then incubated at 55° C. overnight to hybridize the two complementary oligonucleotides.

The following DNA fragments were also isolated. Plasmids pK19/GAPDH-dSsp and -dSna were digested with the restriction enzymes AsuII and SacI and the fragments separated on an agarose gel. The 400 bp and 600 bp fragments were cut out of the gel and electroeluted. Plasmid pDP108 was digested with the restriction enzymes EcoRI and AatII. and the 1.5 kb DNA fragment isolated from the gel. This 1.5 kb pDP108 fragment was mixed with the two AsuII—SacI GAPDH fragments individually, the pK19/ENA3-term 5 kb SacI—AatII purified fragment and the AsuII—EcoRI linker (CAT promoter) and ligated. Transformants were tested both by restriction analysis of small scale DNA preparations, by ice nucleation activity and DNA sequencing. These corresponded exactly, giving plasmids pDP110 (dSsp) and pDP111 (dSna).

Transfer into Yeast expression plasmid

The yeast expression plasmid used to test these constructions was provided by the Biotechnology Department of Ciba-Geigy. This is plasmid pDP34-Xho (pDP34 see European Patent Application No. 89810297.5-. The Xho modification is pDP34 digested with SacI and BamHI and the oligonucleotides used for making pUG21 added, see page 9) which consists of the E. coli vector pUC19, the complete yeast 2 micron plasmid and two yeast selectable auxotrophic markers. The first being the URA3 gene for easy transformation and low copy number selection of the plasmid in yeast, and secondly the dLEU2 allele of the LEU2 gene for induced high copy number.

Figure 4A:
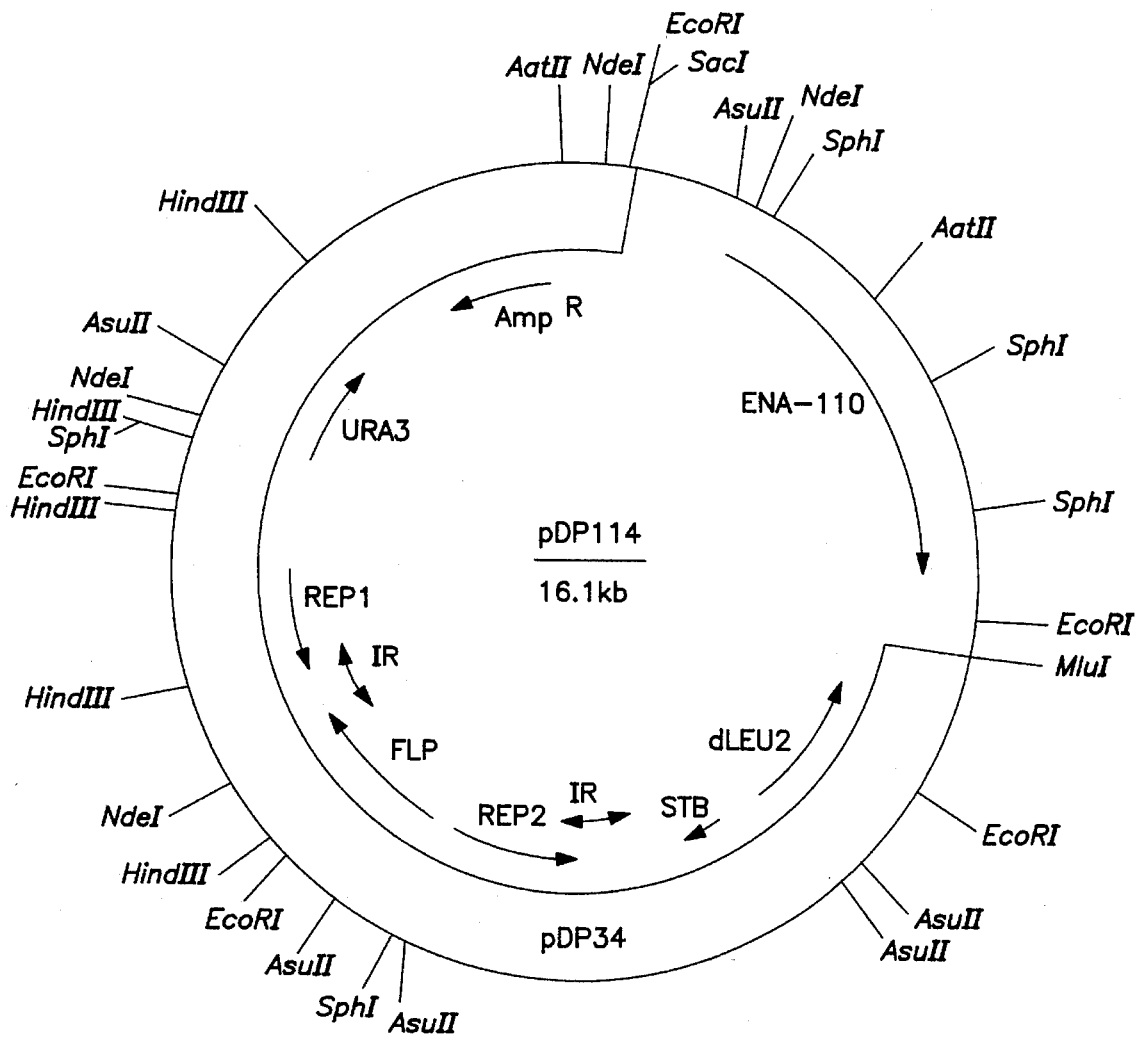
FIG. 4A is a map of the plasmid pDP114.
Figure 4B:
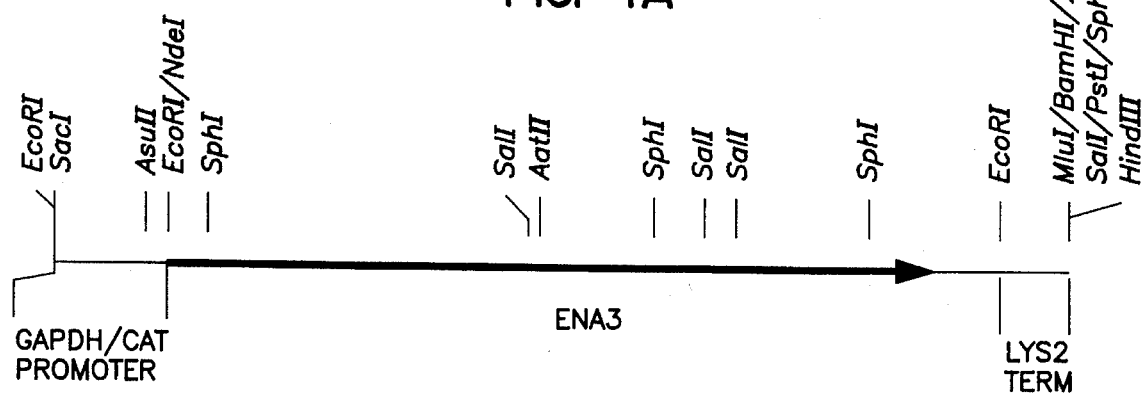
FIG. 4B is a restriction map of ENA-110.
Figure 5A:
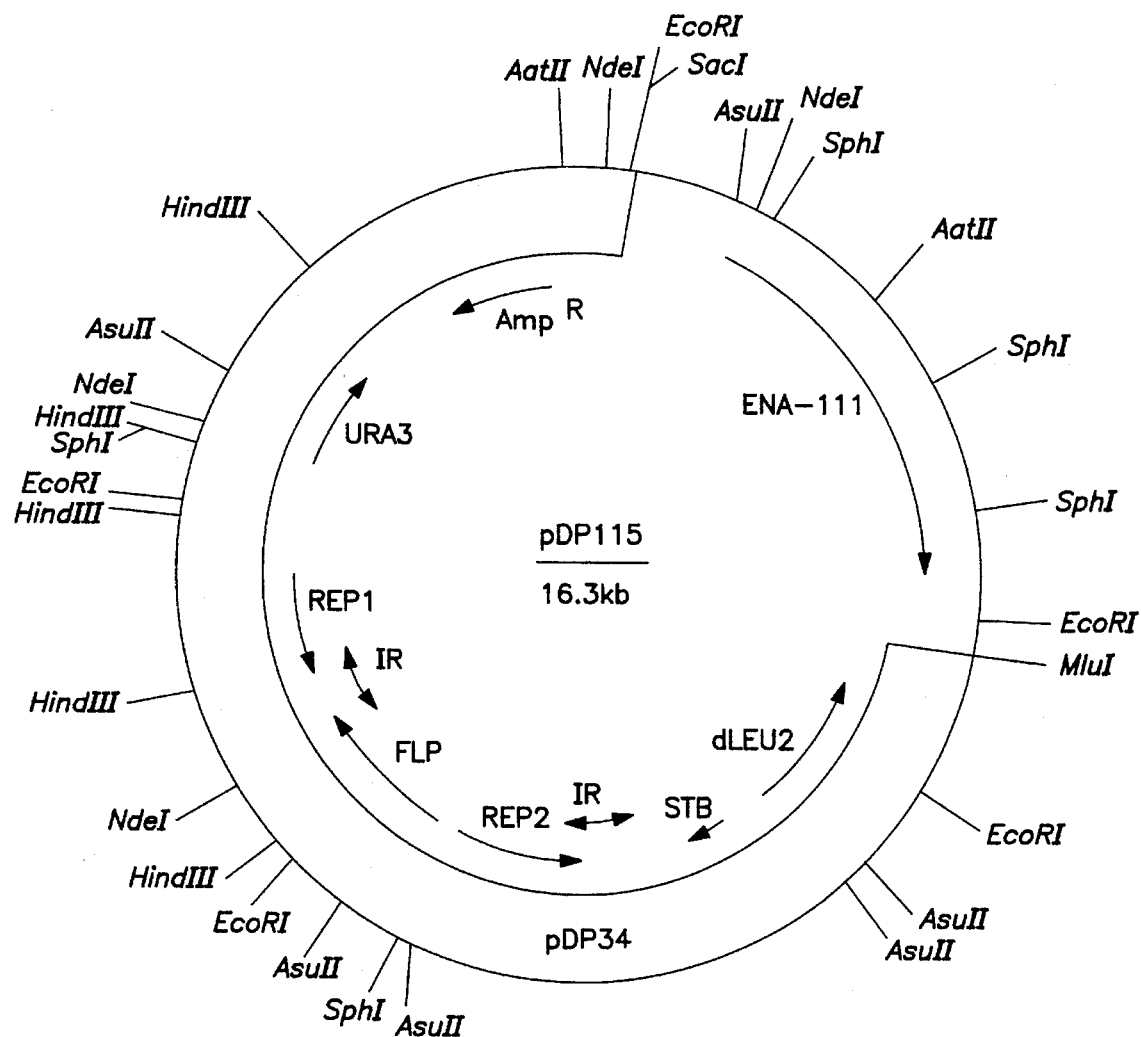
FIG. 5A is a map of the plasmid pDP115.
Figure 5B:
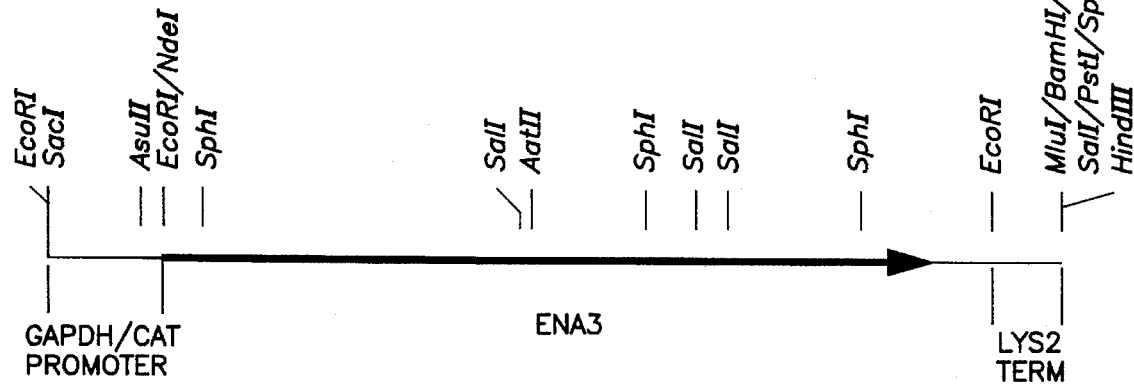
FIG. 5B is a restriction map of ENA-111.
Figure 6:
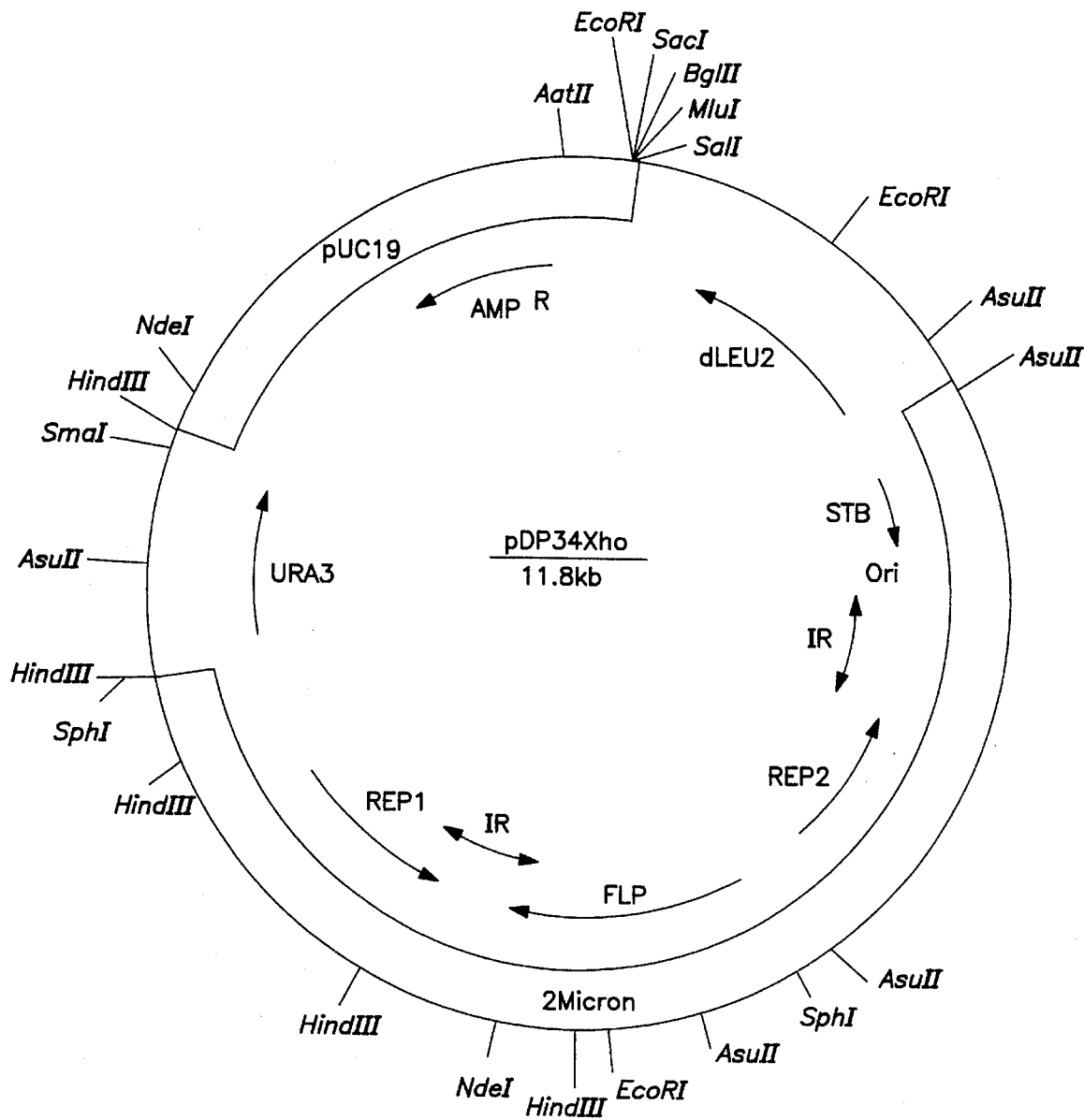
FIG. 6A is a map of the plasmid pDP34Xho.

Plasmid pDP34-Xho was digested with the restriction enzymes SacI and MluI. Plasmids pDP108, 109, 110 and 111 were also digested with the restriction enzymes SacI and MluI. The pDP34 plasmid was ligated to the four plasmid digests individually and transformed into E. coli. Transformants were selected on ampicillin plates to select for the pDP34 plasmid. Restriction analysis identified plasmids pDP112 (containing the ENA3 construction from pDP108), pDP1113 (109), pDP114 (110) and pDP115 (111). Plasmids pDP114, pDP115 and pDP34Xho are shown diagrammatically in FIGS. 4A, 5A and 6 respectively of the accompanying drawings. Restriction maps of ENA-110 (from pDP110) and ENA-111 (from pDP111) are shown in FIGS. 4B and 5B, in which P represents promoter and T represents terminator.

Yeast transformation

Yeast cells are inoculated from an overnight culture in YPD medium (1% Bacto-yeast extract, 2% Bacto-peptone, 2% dextrose) and grown overnight at 30° C.

Take culture at about $OD_{600}$=2.0,

Pellet 50 ml cell suspension at 3,000 rpm for 5 mins,

Discard supernatant and wash cells in 50 ml TE buffer,

Resuspend cells in 20 ml of 1 M Lithium acetate (in TE),

Incubate at 30° C. for 90 mins with gentle shaking,

Pellet cells at 3,000 rpm for 5 mins,

Discard supernatent and resuspend in 1 ml 1 M LiOAc.

200 μl aliquots of competent cells plus 1 μg of DNA,

Incubate at 30° C. for 10 mins,

Add 1 ml of 50% PEG solution (in TE),

Mix and incubate at 30° C. for 60 mins,

Heat shock at 42° C. for 5 mins,

Pellet cells in microfuge with 5 seconds spin,

Discard supernatant,

Resuspend cells in 300 μl 800 mM sorbitol and plate onto selective plates.

Expression of ENA3 gene in yeast

The plasmids pDP112, pDP113, pDP114 and pDP115 were transformed into the yeast strain YP42 (Genotype; α, ura3-52, his4-580, leu2) as described above. Transformants were selected on SD (0.67% Bacto-yeast nitrogen base without amino acids, 2% dextrose) minimal agar plates supplemented with Histidine (20 mg/liter) and Leucine (30 mg/liter) at 30° C. Transformed colonies were streaked out onto the same selective plates twice to single colonies to purify the transformants. Colonies from each plasmid construction were used to inoculate cultures in YPD medium which were grown at 30° C. with agitation. These were grown to early log phase, OD$_{600}$ approximately 1.0 and the cells pelleted, etc.. The ice nucleation spectra of YP42 plus plasmids pDP114 and pDP115 are shown diagrammatically in FIG. 7 and 8 of the accompanying drawings. These figures show log (ice nuclei/cell as ordinate plotted against Supercooling (–°C.) as abscissa for YPD medium (o).

Figure 7:
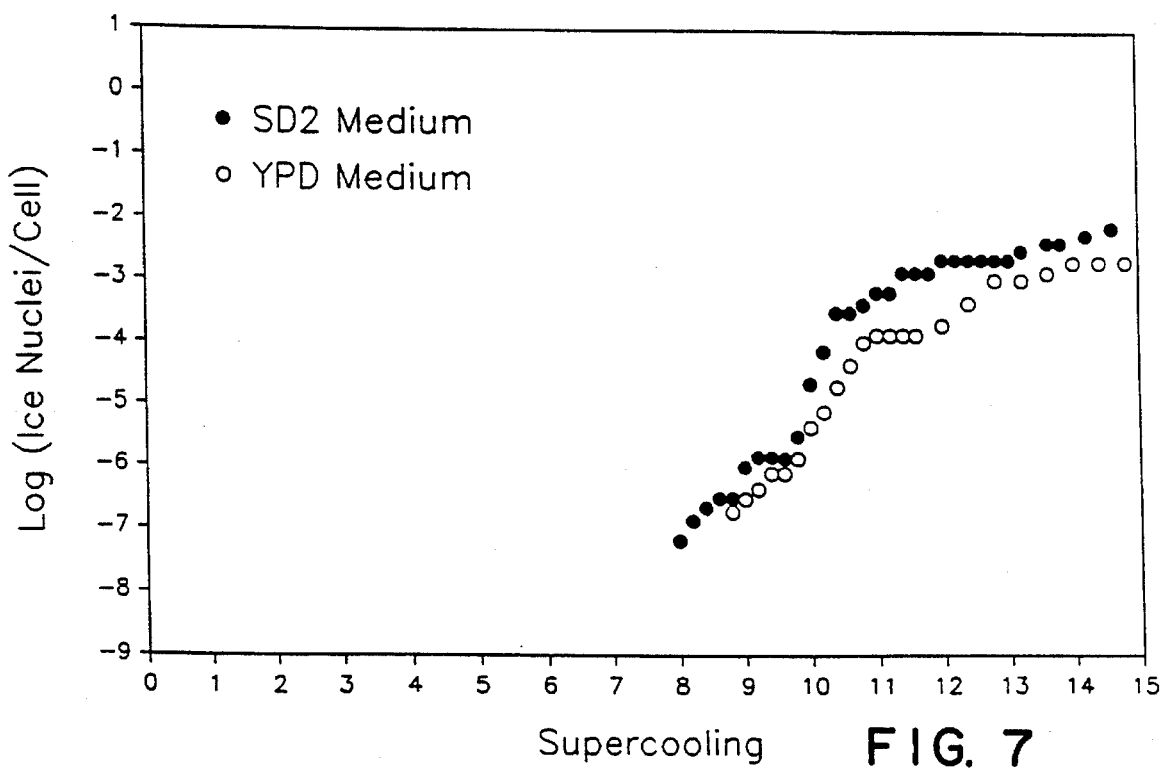
FIG. 7 illustrates the ice nucleating spectra of YP42+ pDP114.
Figure 8:
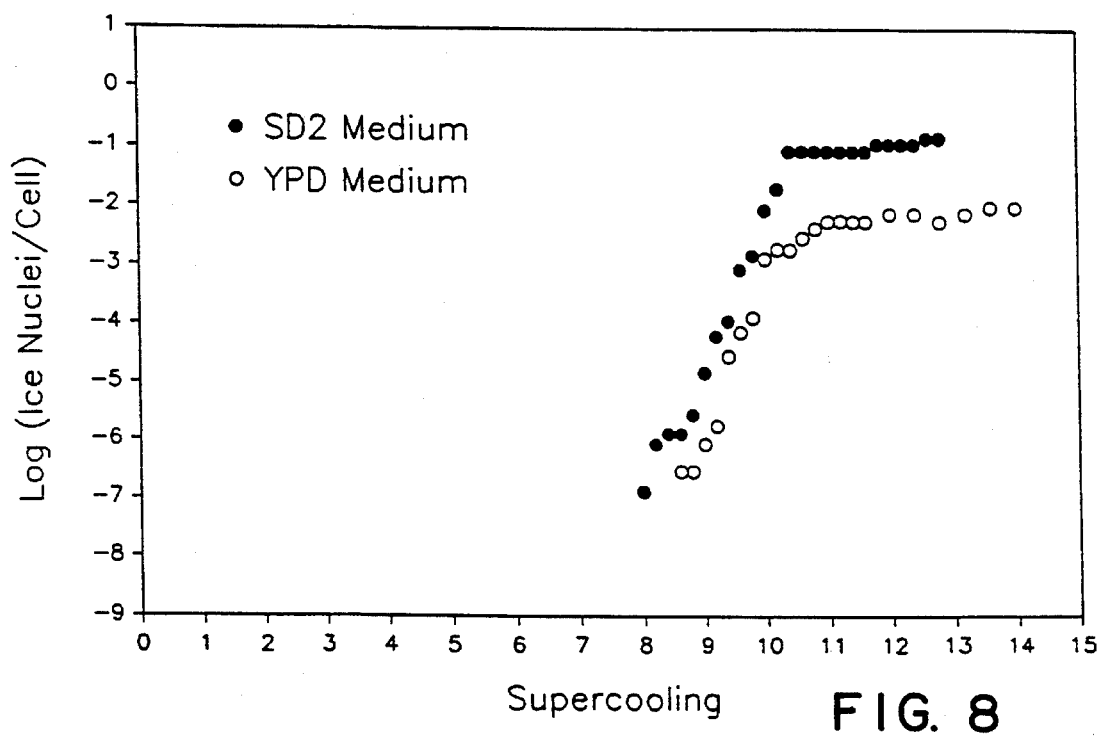
FIG. 8 illustrates the ice nucleating spectra of YP42+ pDP115.

YP42 plus plasmids pDP114 and pDP115 were also grown in SD2 medium (0.67% Bacto-yeast nitrogen base without amino acids, 0.5% casamino acids, 2% dextrose and 50 mM sodium citrate pH 6.0), at 30° C. with agitation. The corresponding freezing spectra for SD2 medium are shown in FIG. 7 and 8 of the accompanying drawings (●).

Construction Of pDP140

Figure 9A:
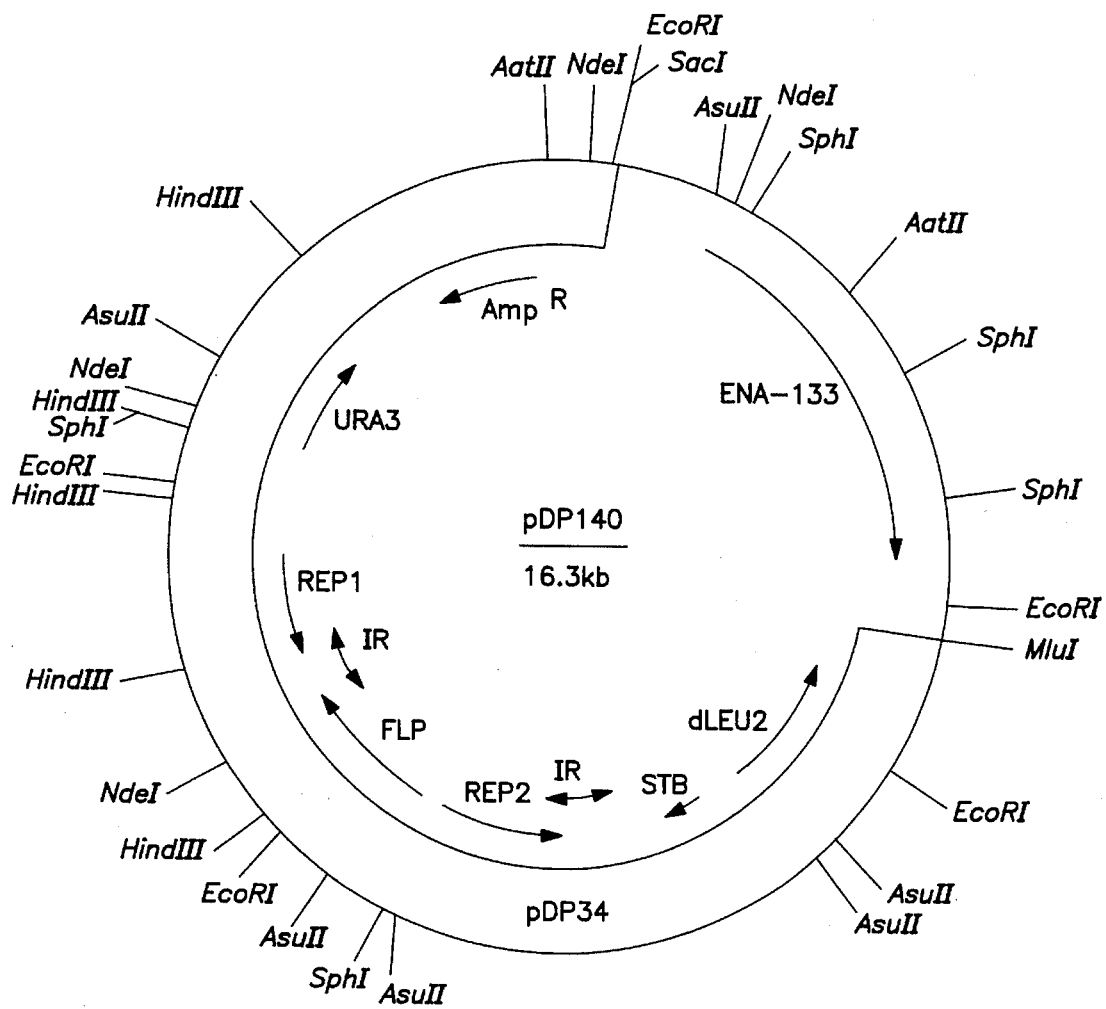
FIG. 9A is a map of the plasmid pDP140.
Figure 9B:
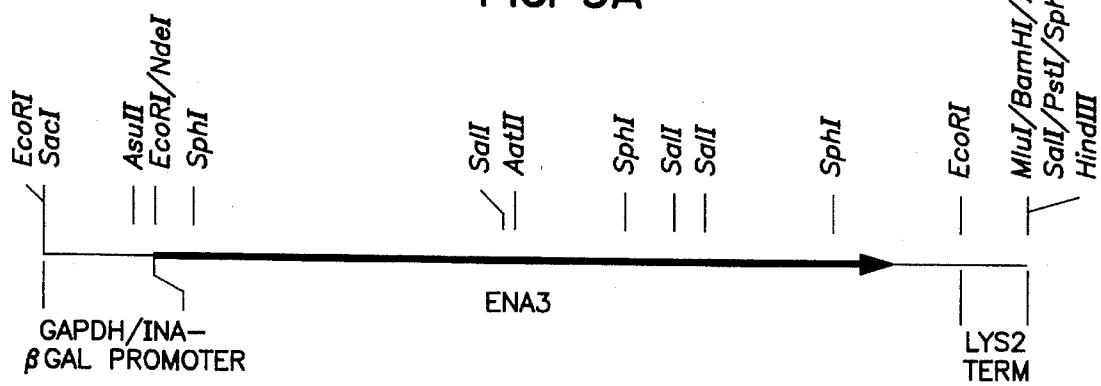
FIG. 9B is a restriction map of ENA-133.
Figure 10:
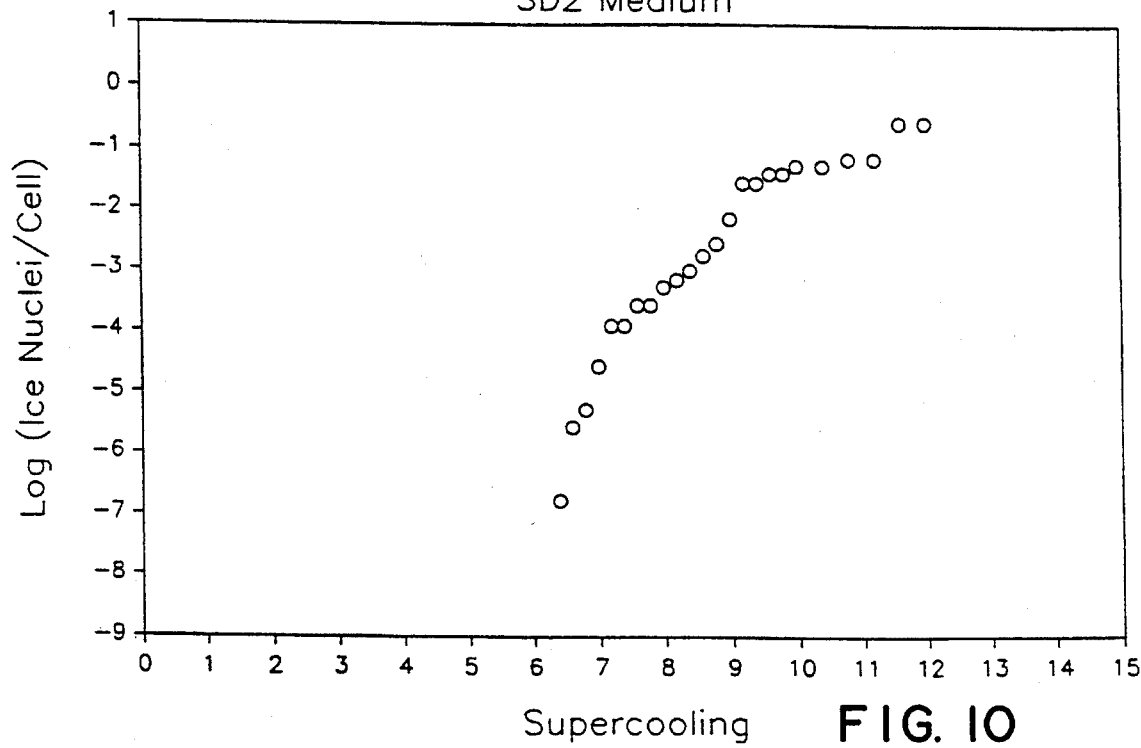
FIG. 10 illustrates the ice nucleating spectra of YP42+ pDP140.

Plasmid pDP133 is described later. This plasmid was digested with the restriction enzymes MluI and SacI, mixed with MluI and SacI digested pDP34Xho and ligated. This was transformed into competent *E. coli* cells and the transformants selected on YT plates supplemented with ampicillin. Colonies were screened by freezing and restriction enzyme analysis to give plasmid pDP140 which is shown diagrammatically in FIG. 9A of the accompanying drawings. FIG. 9B shows a restriction map of ENA-133 (from pDP133), in which P represents promoter and T represents terminator.

pDP140 was transformed into YP42 as described above. Colonies were cultured in SD2 medium at 30° C. with agitation. The freezing spectrum of YP42 plus plasmid pDP140 is shown in FIG. 10 of the accompanying drawings, in which log (ice nuclei/cell) is plotted against supercooling (–°C.).

UBI4 promoter preparation and addition

The starting material is Ciba Geigy's plasmid KS+/UBI4, consisting of the 6 kb genomic SacI fragment from the wild-type yeast strain S288C containing the UBI4 gene (E. Ozkaynak et al., The EMBO Journal, Vol 6, no 5, 1987, 1429–1439) cloned into the SacI site of the Bluescript plasmid KS+ (Stratagene Cloning Systems, USA). Plasmid KS+/UBI4 was digested with the restriction enzymes HindIII and BglII, the fragments resolved on an agarose gel, the 1 kb band was cut out and electro-eluted. Plasmid Bluescript SK+ (Stratagene Cloning Systems, USA) was digested with the restriction enzymes HindIII and BglII. The two DNA fragments were mixed together, ligated and transformed into competent *E. coli* cells. Transformants were selected on YT plates supplemented with ampicillin analyzed by restriction enzyme digestions and the plasmid BA1 identified. The *E. coli* strain containing plasmid BA1 was then infected with the helper phage M13/K07 according to the Stratagene instructions and the single stranded form of BA1 recovered from the supernatant. This was purified for further use.

The UBI4 promoter was modified by oligonucleotide directed site specific mutagenesis to introduce an EcoRV restriction site directly before the 'ATG' of the UBI4 gene as follows;

5'actttaactaatagattATGcagattttcgtcaa3'        [SEQ ID NO:10]

3'AACTAATAGATATCGCAGATTTTCG5'  [SEQ ID NO:11]
           <     >
          EcoRV where the upper sequence is the genomic UBI4 gene around the 'ATG' (indicated by upper case letters) and the lower sequence (in capital letters) is the Oligo 166 used for the mutagenesis (the new EcoRV restriction site being indicated below). The mutagenesis was done with the "Oligonucleotide-directed in vitro mutagenesis system, Version 2" (Amersham, UK) according to the manufacturer's instructions. The transformants were selected on YT plates supplemented with ampicillin, analyzed with the restriction enzyme EcoRV and the plasmid SK+/UBI4EcoRV identified.

Plasmid pDP108 was digested with the restriction enzyme NdeI and the overhang filled in with Klenow enzyme. This was then digested with the restriction enzyme AatII and the fragments resolved on an agarose gel. The 1.5 kb DNA fragment was cut out of the gel and electro-eluted. Plasmid vector pGEM7 (Promega, USA) was digested with the restriction enzymes HindIII and AatII. The pGEM7 vector, the UBI4 promoter and the pDP108 5' ENA3 DNA fragment were mixed and ligated. This ligation was transformed into competent *E. coli* cells and plated onto YT plates supplemented with ampicillin. Transformants were analyzed and the plasmid BF1 identified.

Figure 12:
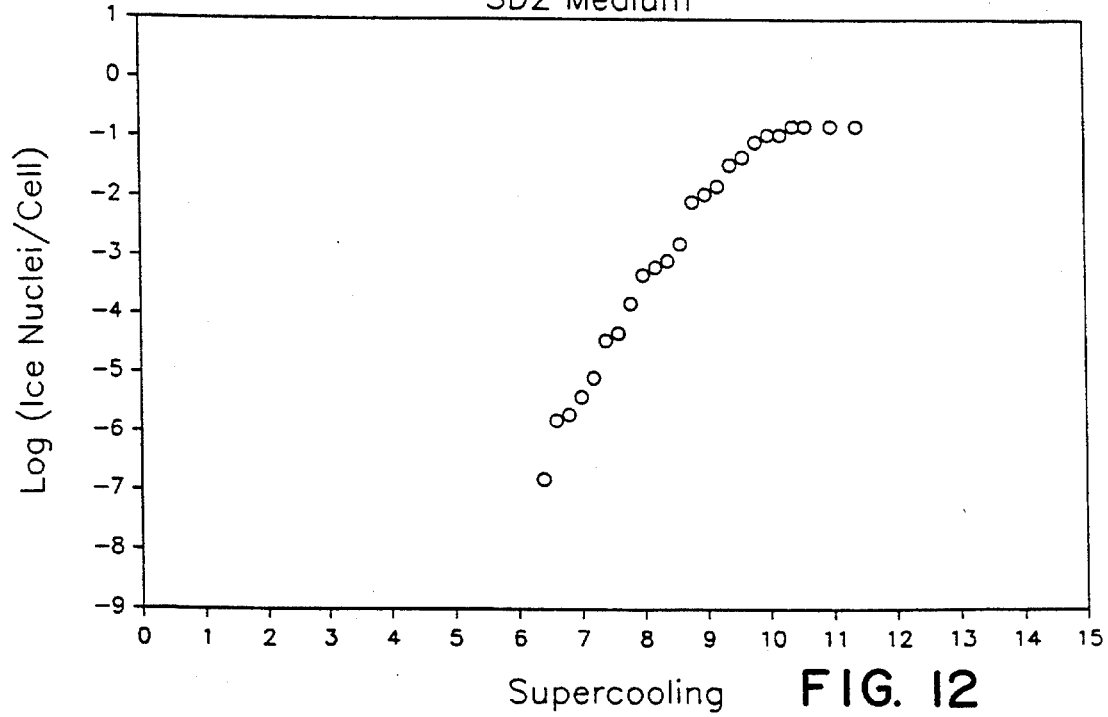
FIG. 12 illustrates the ice nucleating spectra of YP42+ pDP120.
Figure 11A:
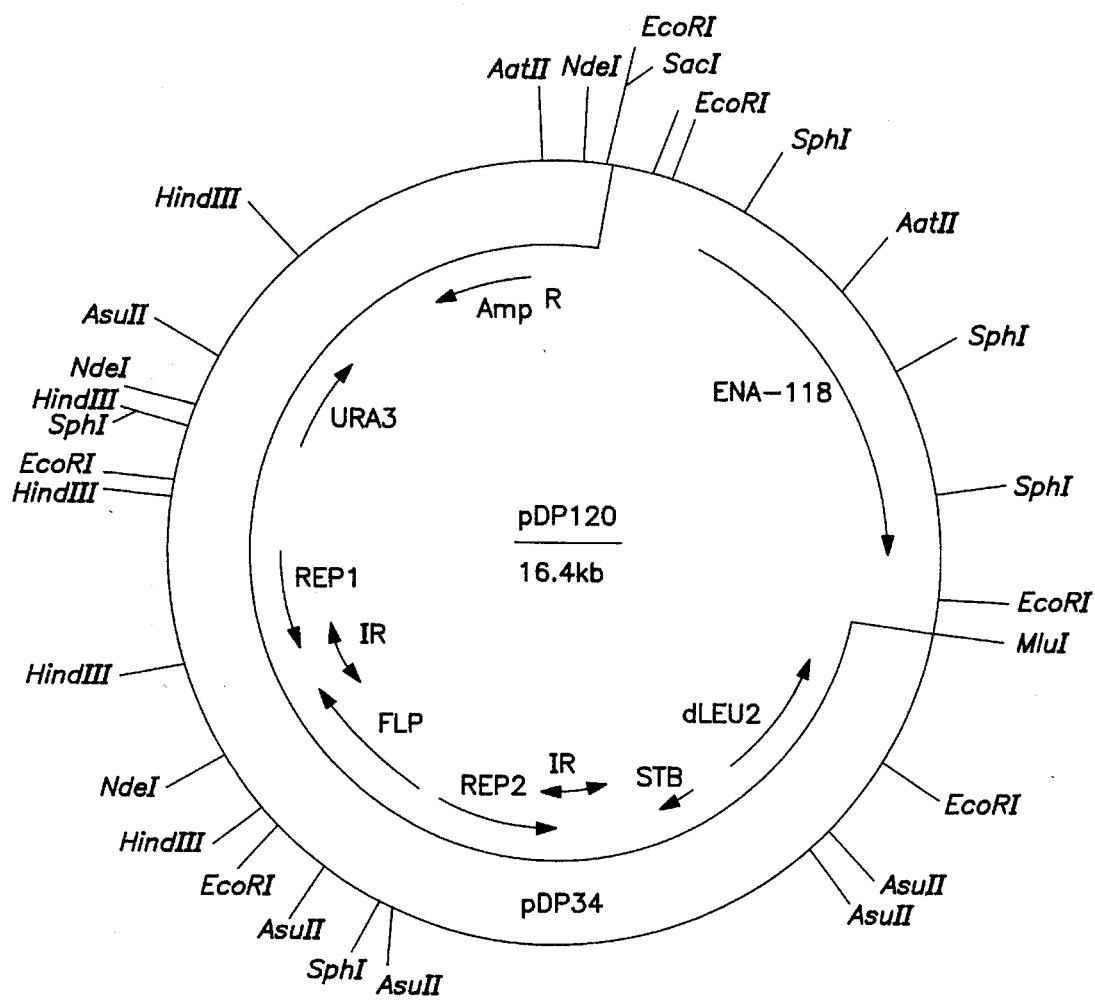
FIG. 11A is a map of the plasmid pDP120.
Figure 11B:
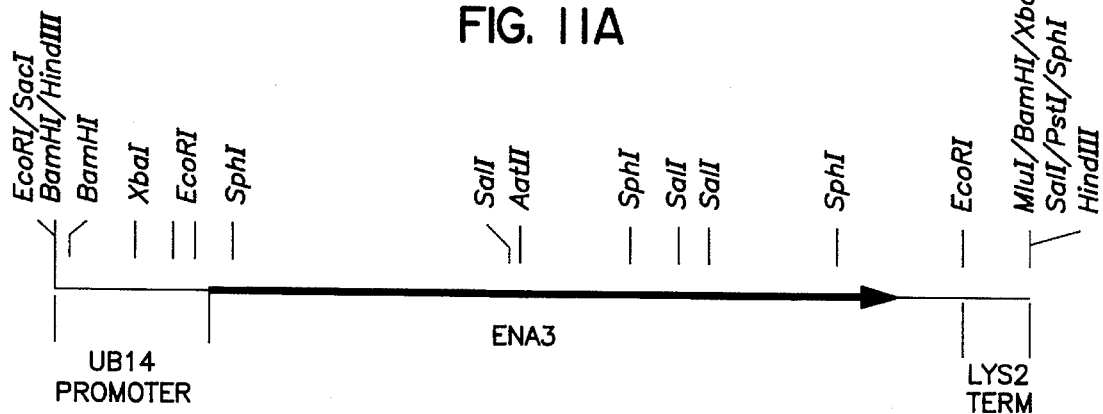
FIG. 11B is a restriction map of ENA-118.

Plasmid BF1 was digested with the restriction enzymes SacI and AatII, the fragments resolved on an agarose gel and the 2 kb fragment was electro-eluted. This was mixed with the previously described 5 kb pK19/ENA3-term, SacI—AatII purified and dephosphorylated fragment, ligated and transformed into competent *E. coli* cells. Transformants were selected on YT plates supplemented with kanamycin and analyzed by restriction enzyme digestions, freezing and DNA sequencing to give plasmid pDP118. The ENA3 insert of pDP118 was then transferred into the yeast expression vector pDP34 to give plasmid pDP120. Plasmid pDP120 is shown diagrammatically in FIG. 11A of the accompanying drawings. FIG. 11B shows a restriction map of ENA-118 (from pDP115), in which P and T respectively represent promoter and terminator.

pDP120 was transformed into YP42 as described above. Colonies were cultured in SD2 medium at 30° C. with agitation. The freezing spectrum of YP42 plus pDP120 is shown in FIG. 12 of the accompanying drawings, in which log (ice nuclei/cell) is plotted against supercooling (–°C.).

Targeting of the ENA3 gene in yeast

To improve the targeting of the ice nucleating protein and potentially it's phenotypic expression we made constructions with native yeast signal sequences fused to the amino terminus of the ENA3 protein. Two were chosen, the PHO5 signal sequence (B. Bajwa et al, Nucleic Acids Research, Vol 12, no 20, 1984, pp 7721–7739), and the alpha factor pre-pro leader sequence (J. Kurjan & I. Herskowitz, Cell 30, 1982, pp 933–943).

PHO5 signal sequence

The PHO5 signal sequence was achieved by the synthesis of two complementary oligonucleotides that act as a linker, while containing the required amino acid sequences as follows (The synthetic oligonucleotides are indicated in capital letters):

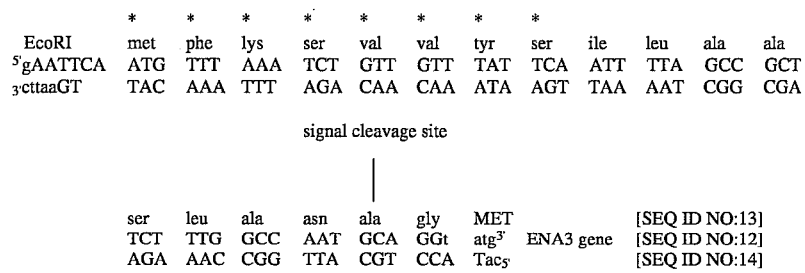

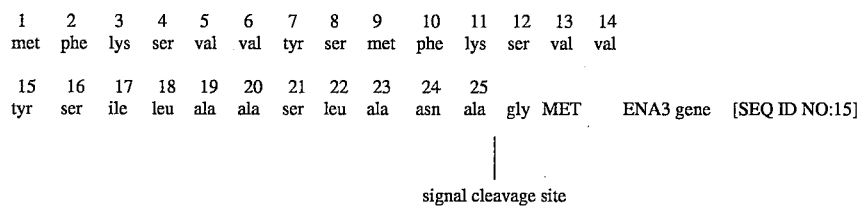

Figure 13A:
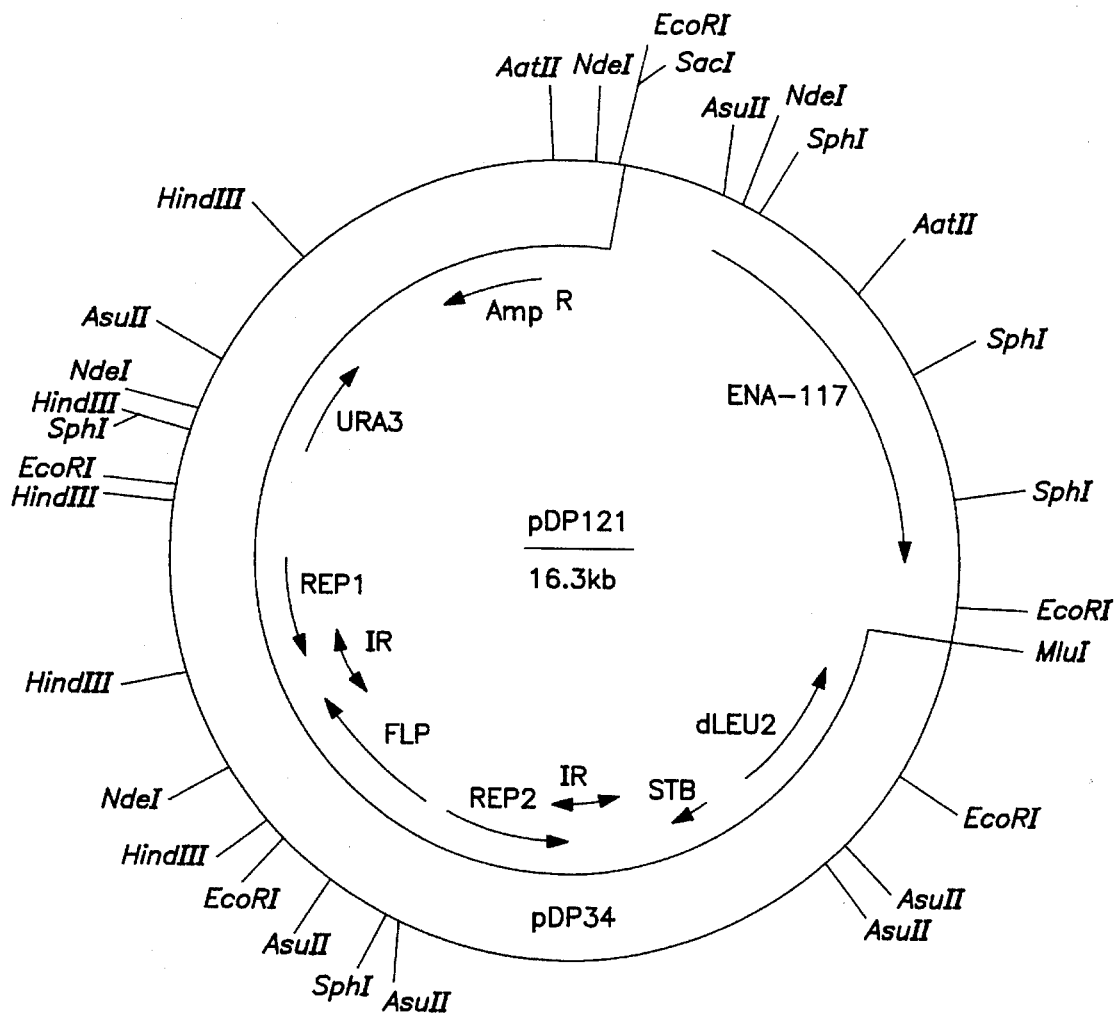
FIG. 13A is a map of the plasmid pDP121.
Figure 13B:
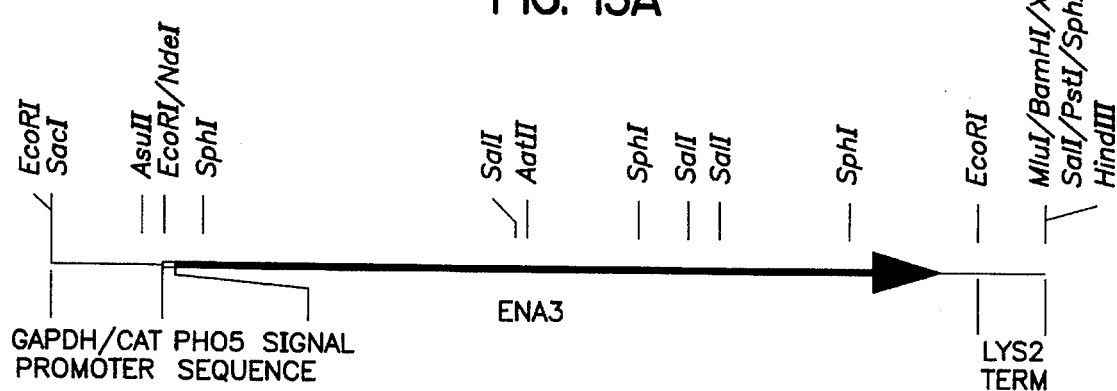
FIG. 13B is a restriction map of ENA-117.

The upper oligonucleotide is oligo 174 (59 mer) and lower is oligo 175 (57 mer). These two oligonucleotides were mixed together in approximately equimolar amounts and hybridized in a high salt solution. These hybridized oligonucleotides were mixed with the following purified fragments; the previously described pK19/ENA3- term 5 kb, SacI and AatII digested, gel purified and dephosphorylated fragment; the 700 bp SacI and EcoRI digested and gel purified fragment of pDP111; and the 1.45 kb NdeI and AatII digested and gel purified fragment of pDP111. This was ligated and transformed into *E. coli*. Transformants were selected initially by their activity in *E. coli* and secondly by restriction enzyme analysis giving plasmid pDP117 and in pDP34 plasmid pDP120. DNA sequence analysis showed that a portion of the PHO5 signal sequence was duplicated. The 8 amino acids marked by (*, see above) are duplicated giving the following signal sequence;

Plasmid pDP121 is shown diagrammatically in FIG. 13A of the accompanying drawings. FIG. 13B shows a restriction map of ENA-117 (from pDP117), in which P, SS and T respectively represent promoter, signal sequence and terminator.

Figure 14:
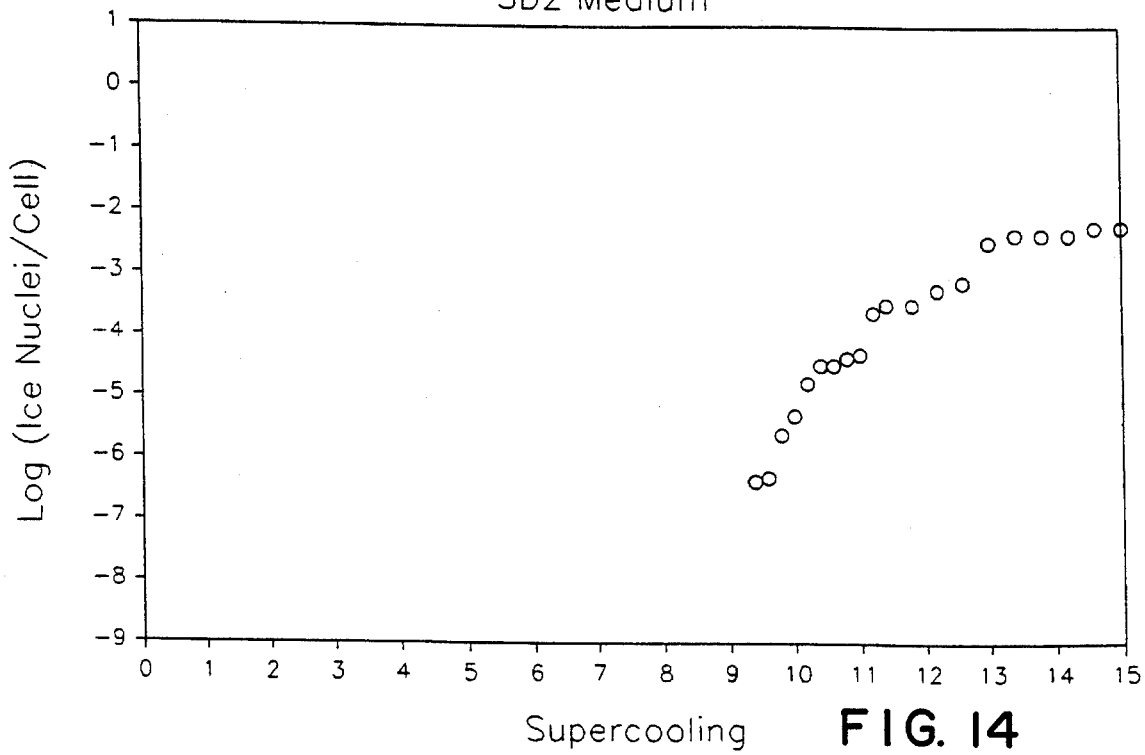
FIG. 14 illustrates the ice nucleating spectra of YP42+ pDP121.

Plasmid pDP121 was transformed into the yeast strain YP42 and colonies selected on SD+HIS+LEU plates. Cultures of the transformants were grown in SD2 medium and assayed for ice nucleation activity. The freezing spectrum of YP42 plus pDP121 is shown in FIG. 14 of the accompanying drawings, in which log (ice nuclei/cell) is plotted against supercooling (−°C.).

Alpha factor leader

The starting material for the pre-pro-alpha factor leader is Ciba Geigy's pUC/PHO5-alpha factor leader plasmid. This has been modified to contain an EcoRI restriction site, 8bp of the PHO5 promoter followed by the 'ATG' and alpha factor leader. The pre-pro cleavage region has also been modified, with the inclusion of a BglII restriction site at the KEX2 cleavage site, and a PvuII restriction site 6 bp before this (a Chiron Corp. modification).

Figure 16:
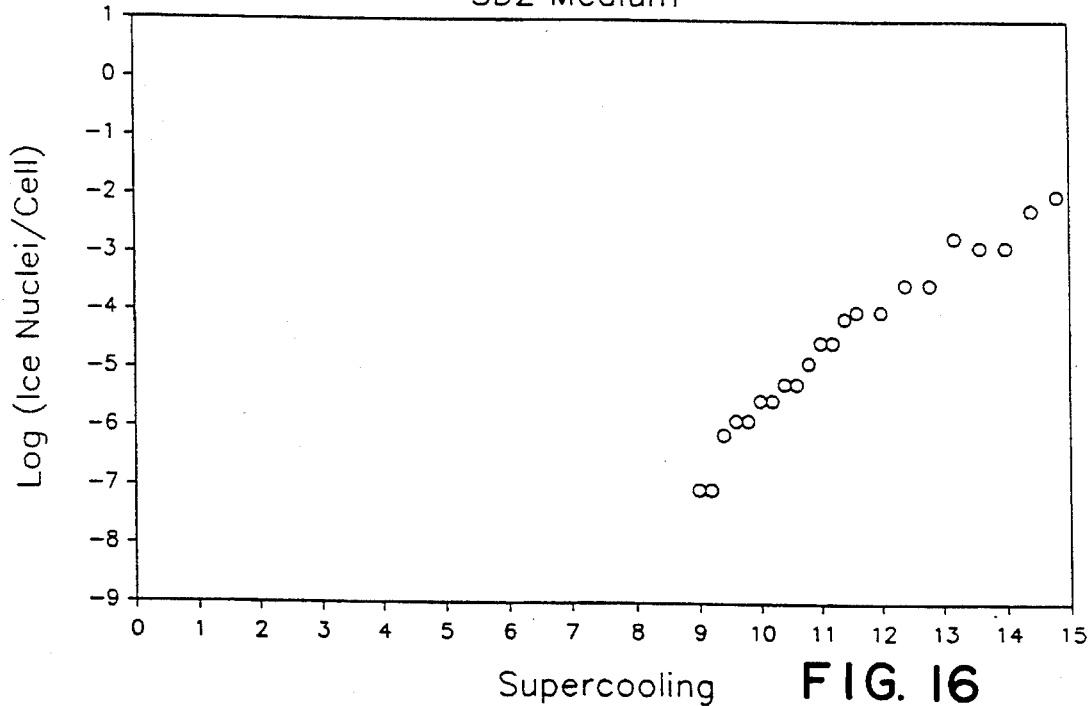
FIG. 16 illustrates the ice nucleating spectra of YP42+ pDP129.
Figure 15A:
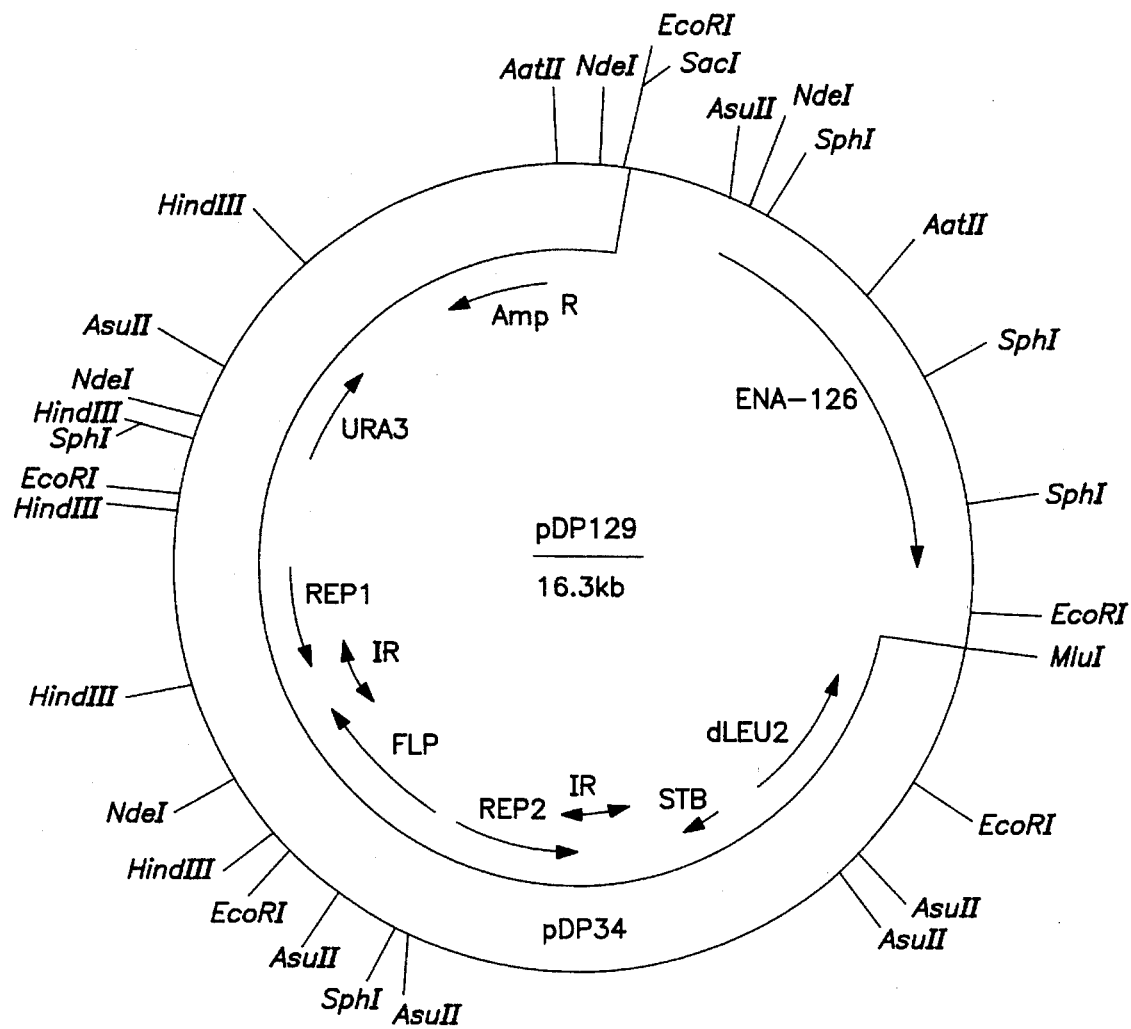
FIG. 15A is a map of the plasmid pDP129.
Figure 15B:
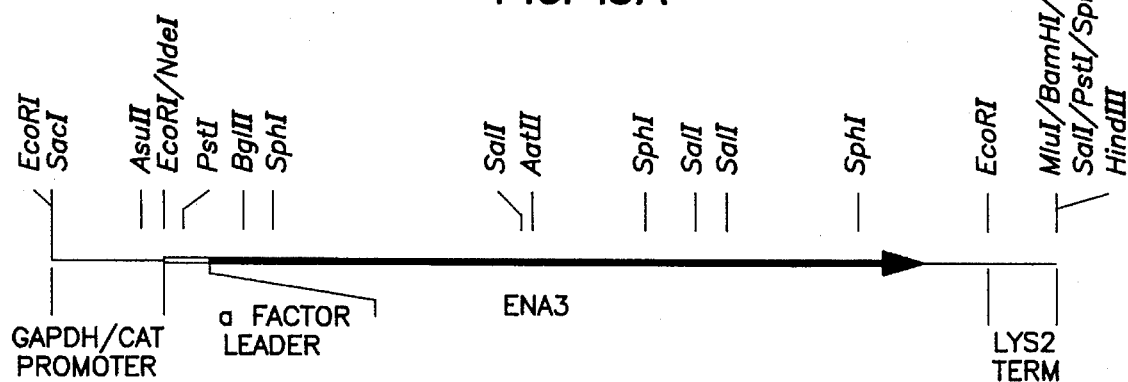
FIG. 15B is a restriction map of ENA-126.

Plasmid pUC/PHO5-alpha factor leader was digested with the restriction enzymes EcoRI and HindIII and the fragments separated on an agarose gel. The 300 bp fragment was cut out and electroeluted. Plasmid pDP111 was digested with the restriction enzymes EcoRI and SacI and the fragments separated on an agarose gel. The 650 bp fragment was cut out and electroeluted. These two components of the alpha factor leader and the GAPDH-dSna-CAT promoter respectively were mixed together with pUC19 digested with the restriction enzymes SacI and HindIII, ligated and transformed into *E. coli*. Transformants were analyzed and the plasmid pUC/GAPDH- dSna-CAT-alpha factor leader identified. Plasmid pUC/GAPDH-dSna-CAT-alpha factor leader was digested with the restriction enzyme BglII and the 5' overhang filled in with Klenow enzyme. This was then digested with the restriction enzyme SacI and the fragments separated on an agarose gel. The 940 bp fragment was cut out and electroeluted. Plasmid pDP111 was digested with the restriction enzyme NdeI and the 5' overhang filled in with Klenow enzyme. This was then digested with the restriction enzyme AatII and the fragments separated on an agarose gel. The 1400 bp fragment was cut out and electroeluted. These two purified fragments were mixed with the pK19/ENA3-term 5 kb, SacI and AatII digested, gel purified and dephosphorylated fragment, ligated and transformed into *E. coli*. Transformants were screened initially for ice nucleating activity, secondly, by restriction enzyme analysis and finally by DNA sequence analysis to identify plasmid pDP126. The insert was then transferred into pDP34 for testing in yeast, giving plasmid pDP129 which is shown diagrammatically in FIG. 15A of the accompanying drawings. FIG. 15B shows a restriction map of ENA-126 (from pDP126), in which P, T and L represent promoter, terminator and leader respectively. Plasmid pDP129 was transformed in the yeast strain YP42 as described above. Transformants were used to inoculate cultures of SD2 medium and incubated at 30° C. with agitation. The freezing spectrum of YP42 plus plasmid pDP129 is shown diagrammatically in FIG. 16 of the accompanying drawings, in which log (ice nuclei/cell) is plotted against supercooling (−°C.).

Alpha factor leader plus linker

Present information on the use of the alpha factor leader for the production of recombinant proteins in yeast has implied an additional requirement. In the native alpha factor the pre-pro peptide is followed by an 8 amino acid linker and then the alpha factor peptide. The linker-alpha factor arrangement is repeated 5 times in the gene and the linkers are removed during processing of the alpha factor. The information implies that the linker should be added after the pre-pro leader and before the gene of interest. This has been done with the help of synthetic oligonucleotides as linkers to insert the required amino acids.

Figure 17A:
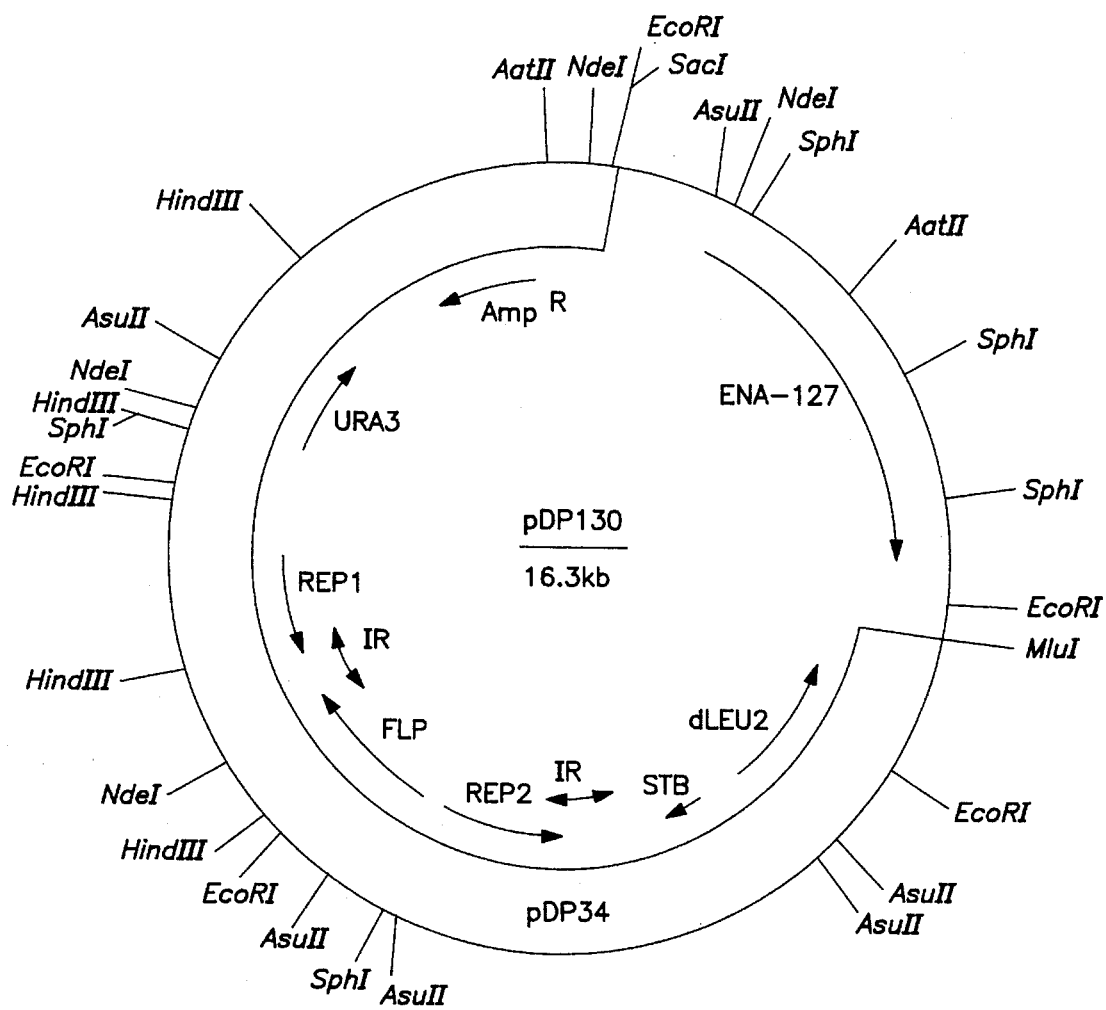
FIG. 17A is a map of the plasmid pDP130.
Figure 17B:
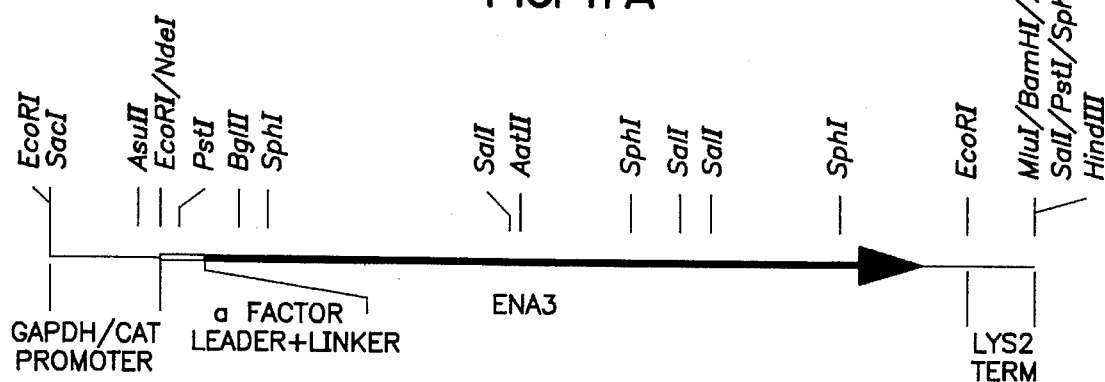
FIG. 17B is a restriction map of ENA-127.
Figure 18:
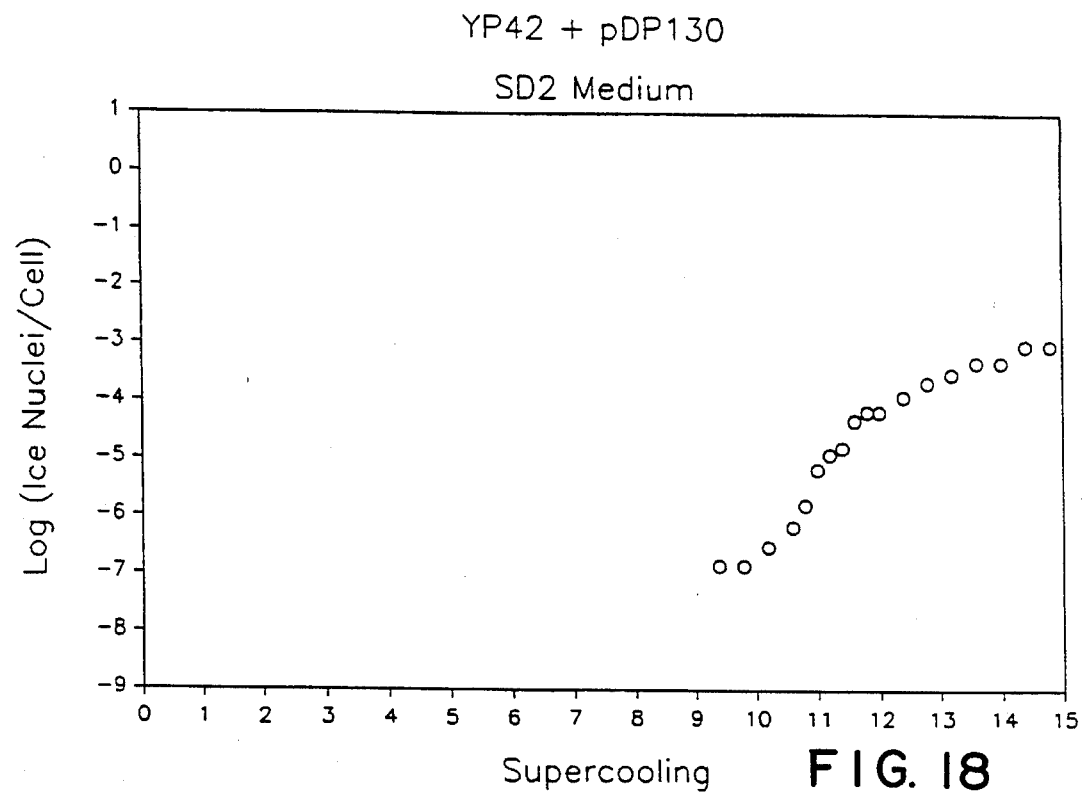
FIG. 18 illustrates the ice nucleating spectra of YP42+ pDP130.

Plasmid pUC/GAPDH-dSna-CAT-alpha factor leader was digested with the restriction enzymes SacI and BglII and the fragments separated on an agarose gel. The 940 bp fragment was cut out and electroeluted. Plasmid pDP111 was digested with the restriction enzymes NdeI and AatII and the fragments separated on an agarose gel. The 1400 bp fragment was cut out and electroeluted. The two purified fragments were mixed with the two hybridized oligonucleotides 208 and 209 and pK19/ENA3-term SacI— AatII fragment described previously, ligated and transformed into $E.$ coli. Transformants were screened by restriction enzyme digestions and DNA sequence analysis to identify plasmid pDP127 which also shows ice nucleation activity. The insert was transferred into the yeast expression plasmid pDP34 giving plasmid pDP130 which is shown diagrammatically in FIG. 17A of the accompanying drawings. FIG. 17B shows a restriction map of ENA-127 (from pDP127) in which P, T and L respectively represent promoter, terminator and leader+ linker. Plasmid pDP130 was transformed into YP42 as described above. Transformants were used to inoculate cultures of SD2 medium and grown at 30° C. with agitation. The freezing spectrum of YP42 plus plasmid pDP130 is shown in FIG. 18 of the accompanying drawings, in which log (ice nuclei/cell) is plotted against supercooling (–°C.).

Targeting to the vacuole

The above described cases only add a native yeast signal sequence to the ENA3 protein and may or may not aid in the targeting of the protein to the membranes, probably via the endoplasmic reticulum. Once a protein enters the endoplasmic reticulum the default pathway is that of secretion out of the cell, or possibly in our case insertion into the outer membrane. Here we target the ENA3 protein to a specific organelle within the cell, namely the vacuole.

The protein carboxy-peptidase Y (CPY) is directed to the vacuole (L. A. Valls et al, Cell 48, 1987, pp 887–897) in a pre- pro form that is processed within the vacuole by proteinase B (the PEP4 gene product). It has also been shown that the sequences required for the targeting are localized within the pre-pro leader sequence. We therefore insert this in front of the ENA3 protein.

The starting material is Ciba Geigy's pBR322/PHO5-pre-pro CPY plasmid. Synthetic oligonucleotides are required as a specific linker between the GAPDH/CAT promoter and the natural StuI restriction site approximately 35 bp into the CPY pre peptide;

```
                              .StuI.
EcoRI     MetLysAlaPheThrSerLeuLeuCysGlyLeuGlyLeu              [SEQ ID NO:17]

5'gAATTCATATGAAAGCATTCACCAGTTTACTATGTGGACTAGGcctg3'           [SEQ ID NO:16]

3'cttaaGTATACTTTCGTAAGTGGTCAAATGATACACCTGATCCggac5'           [SEQ ID NO:18]
```

The oligonucleotides synthesized are shown in capital letters and are Oligo 206 (upper) and Oligo 207 (lower). Plasmid pBR322/PHO5- pre-pro CPY was digested with the restriction enzymes HindIII and StuI and the fragments separated on an agarose gel. The 800 bp fragment was cut out, electroeluted and mixed with hybridized Oligos 206 and 207, and EcoRI and HindIII digested pUG19 plasmid and ligated together. This was transformed into $E.$ coli and transformants were screened by restriction enzyme analysis to give plasmid pUC19/CPY(p-p). Plasmid pUC19/CPY(p-p) was digested with the restriction enzymes EcoRI and HincII, the fragments resolved on an agarose gel and the 340 bp fragment cut out and electroeluted. This fragment was mixed with EcoRI and HincII digested pUC18, ligated and transformed into competent $E.$ coli. Colonies were screened and the plasmid pUC18/pre-pro-CPY identified.

Figure 19A:
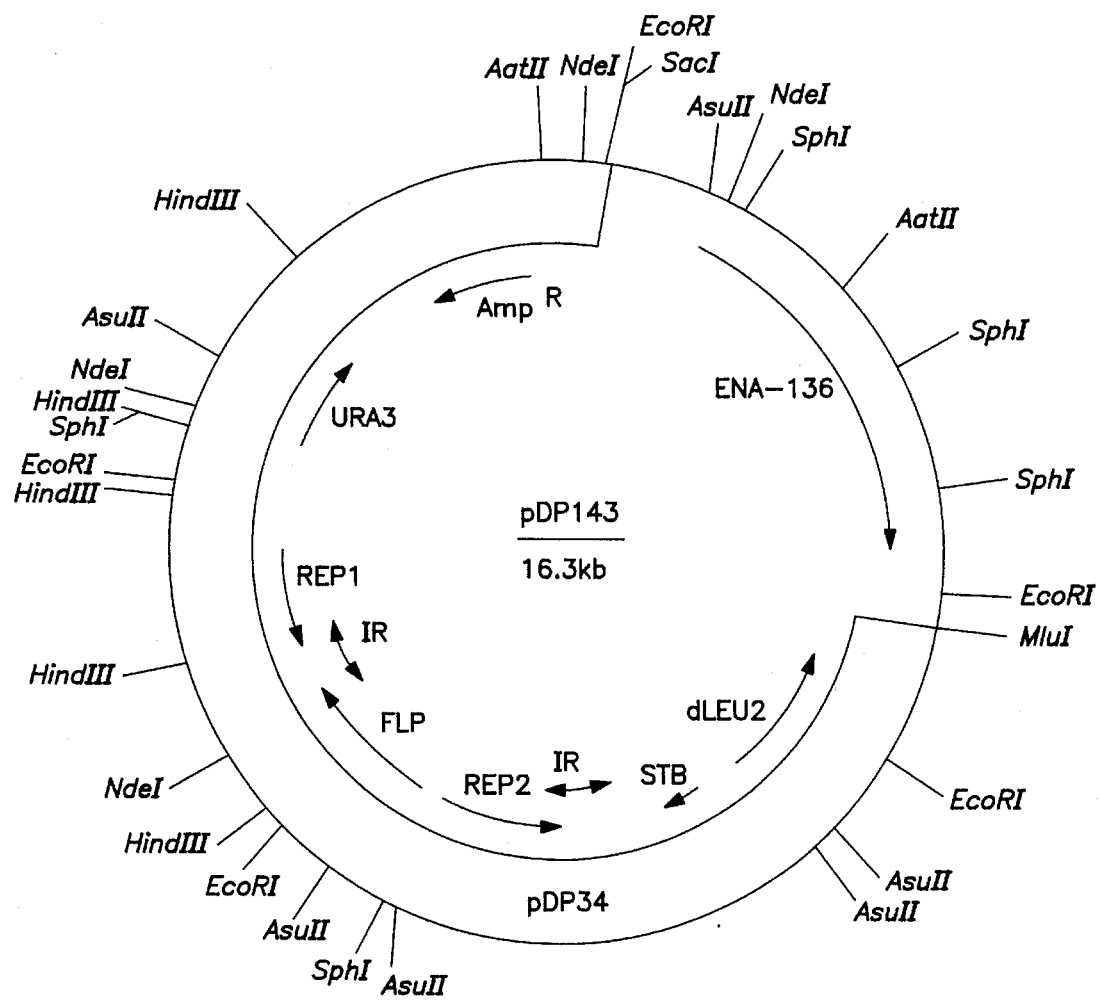
FIG. 19A is a map of the plasmid pDP143.
Figure 19B:
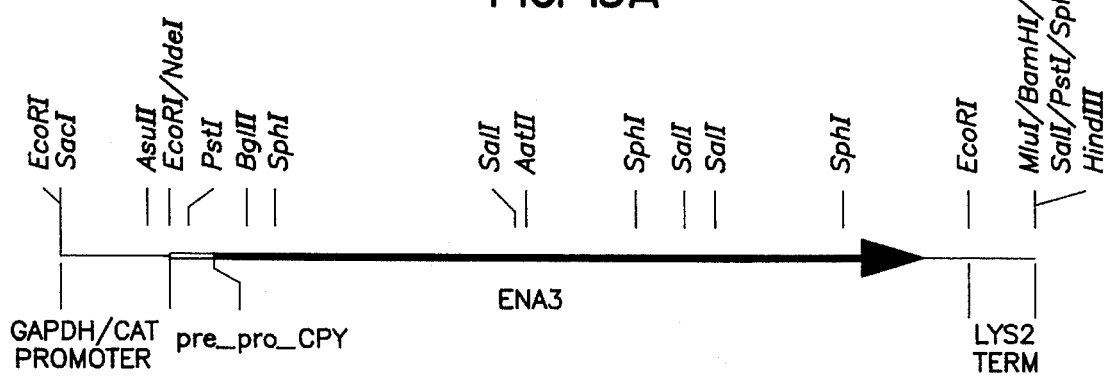
FIG. 19B is a restriction map of ENA-136.

Plasmid pUC18/pre-pro-CPY was digested with the restriction enzymes EcoRI and HindIII and the products resolved on an agarose gel. The 350 bp fragment was cut out and electroeluted. To this was added the gel purified 680 bp SacI EcoRI GAPDHdSna/CAT promoter from plasmid pDP110 and SacI plus HindIII digested pUG19 ligated and transformed into competent $E.$ coli. Colonies were screened and the plasmid pUC18/GAPDHdSna-CAT-pre-pro-CPY identified. Plasmid pUC18/GAPDHdSna-CAT-pre-pro-CPY was digested with the restriction enzyme SalI and the overhang filled in with Klenow enzyme. This was then digested with SacI and the fragments separated on an agarose gel. The 750 bp fragment was cut and electroeluted. Plasmid pDP108 was digested with the restriction enzyme NdeI and the overhang filled in with Klenow enzyme. This was then digested with AatII and the fragments resolved on an agarose gel. The 1500 bp fragment was cut out and electroeluted. These two isolated fragments were mixed with the previously described pK19/ENA3-term 5 kb, SacI and AatII digested, gel purified and dephosphorylated fragment, ligated and transformed into competent $E.$ coli. Colonies were screened by restriction enzyme analysis and by freezing, both of which identified the same plasmids, pDP136. The insert of plasmid pDP136 was transferred into the yeast expression plasmid pDP34 to give plasmid pDP143 which is shown in FIG. 19A of the accompanying drawings. FIG. 19B shows a restriction map of ENA-136 (from pDP136) in which P and T respectively represent promoter and terminator.

Figure 20:
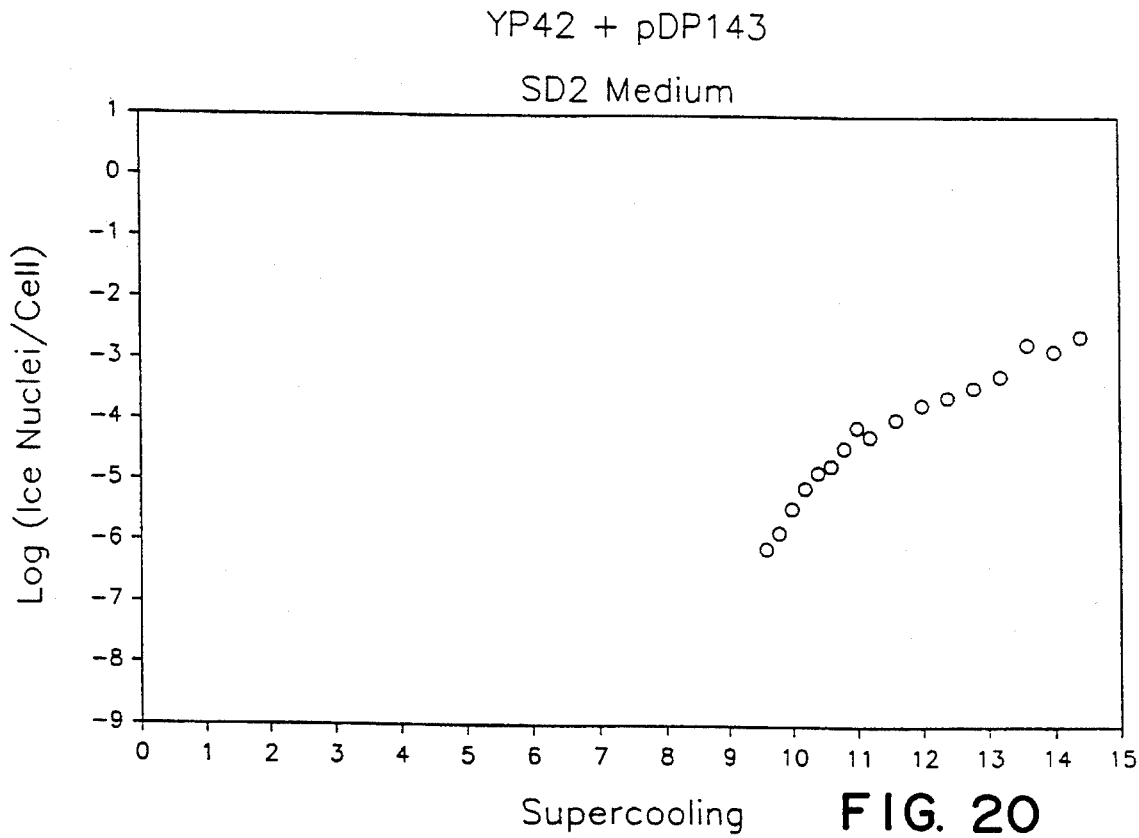
FIG. 20 illustrates the ice nucleating spectra of YP42+ pDP143.

Plasmid pDP143 was transformed into YP42 as described above. Transformants were used to inoculate cultures of SD2 medium and incubated at 30° C. with agitation. The freezing spectrum of YP42 plus plasmid pDP143 is shown in FIG. 20 of the accompanying drawings, in which log (ice nuclei/cell) is plotted against supercooling (–°C.).

Example 4

Expression in Lactococcus lactis

Expression of the ENA3 gene from it's native Pseudomonas promoter has been tried without success (data not shown), even though the important –35 and –10 regions are very similar to the Lactococcus lactis phospho-β-galactosidase promoter (B. Boizet et al., Gene 62, 1988, 249–261) (data not shown). But what may be of importance is the presence of a possible mRNA leader of 60–65 base pairs directly before the initiating 'ATG'. We tested this by constructing a hybrid promoter with the −35 and −10 sequences from the ENA3 promoter and the potential leader from the phospho-β-galactosidase promoter. This was done by the use of synthetic oligonucleotides as depicted below:

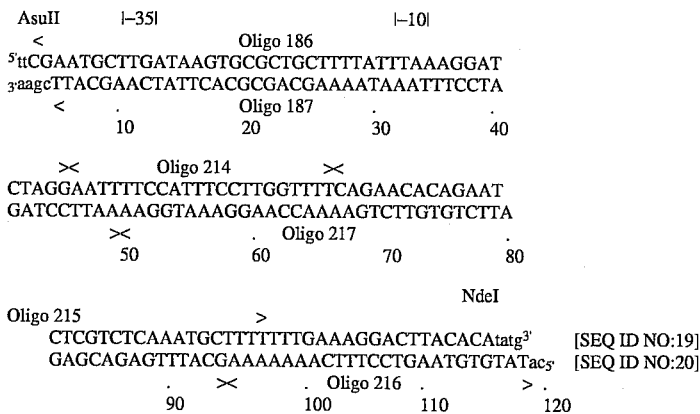

base pair 1 to 45 is the modified ENA3 promoter. Base pair 46 to 115 is the corresponding sequence from the phospho-β-galactosidase gene. From base pair 146 to 120 follows the recognition site for the restriction enzyme NdeI, including the 'ATG' for the ENA3 gene. The synthetic oligonucleotides are shown in capital letters.

The oligonucleotides were kinased and hybridized to each other as described. Plasmid pDP108 was digested with the restriction enzymes NdeI and AatII and the fragments separated on an agarose gel. The 1.5 kb fragment containing the 5' end of the ENA3 gene was cut out and electro-eluted. This DNA fragment was mixed with the synthetic oligonucleotides above, the previously described SacI—AsuII 600 bp yeast promoter fragment from pK19/GAPDH-dSna and the 5 kb SacI—AatII purified and phosphatased fragment from pK19/ENA3-term and ligated. This ligation was transformed into competent E. coli cells and plated onto YT plates supplemented with kanamycin. Transformants were screened by restriction enzyme digestions, ice nucleation activity and DNA sequencing to identify the plasmid pDP133.

Figure 21:
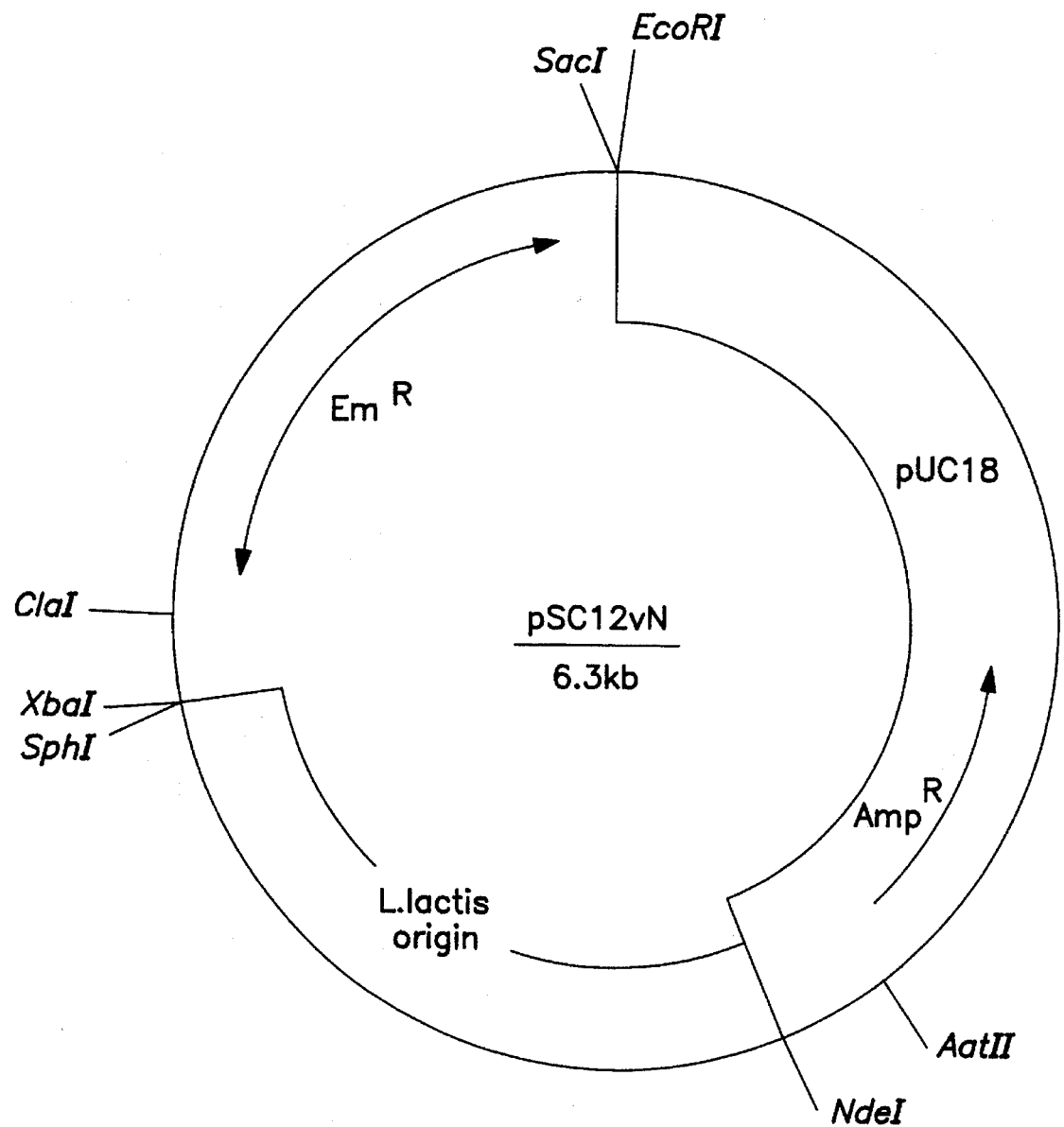
FIG. 21 is a map of the plasmid pSC12vN.
Figure 22A:
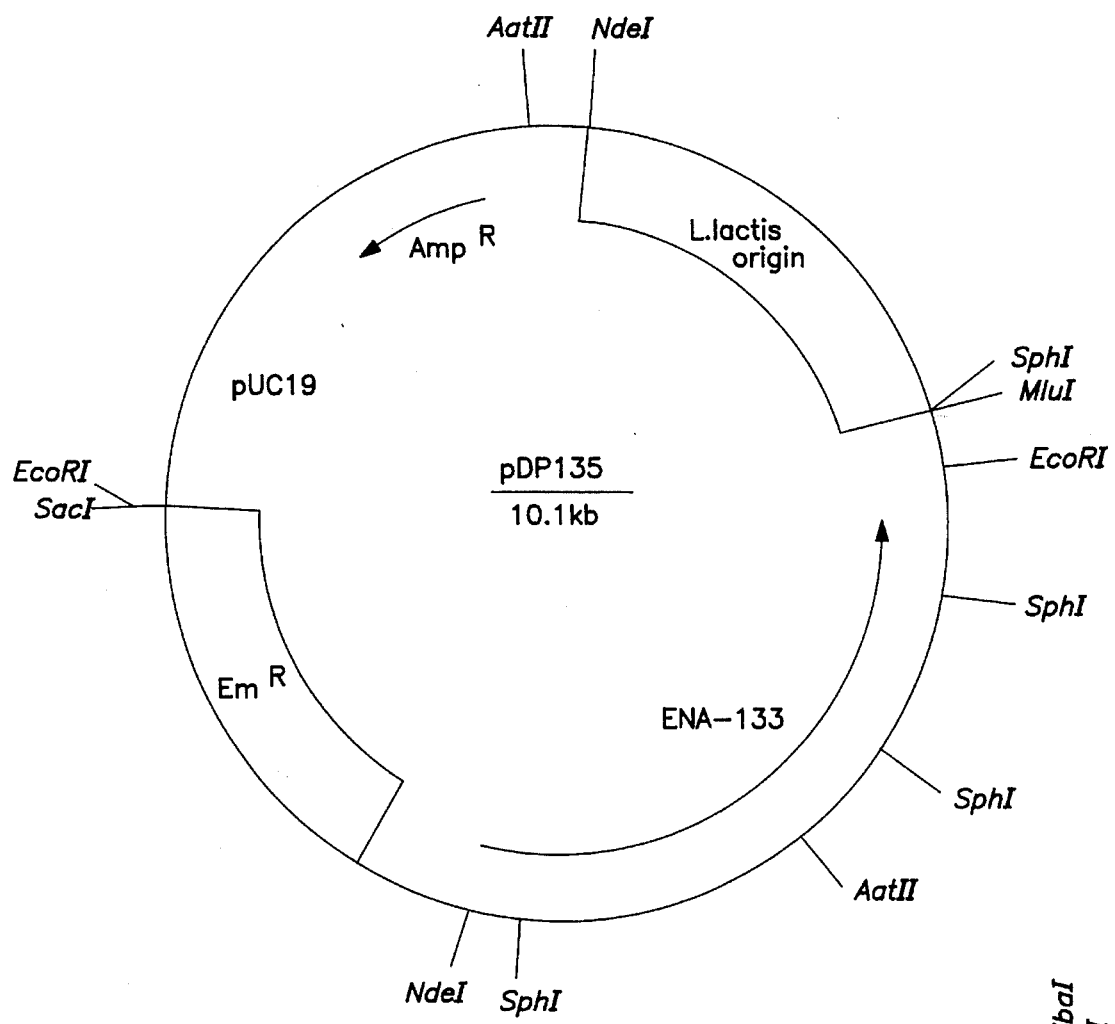
FIG. 22A is a map of the plasmid pDP135.
Figure 22B:
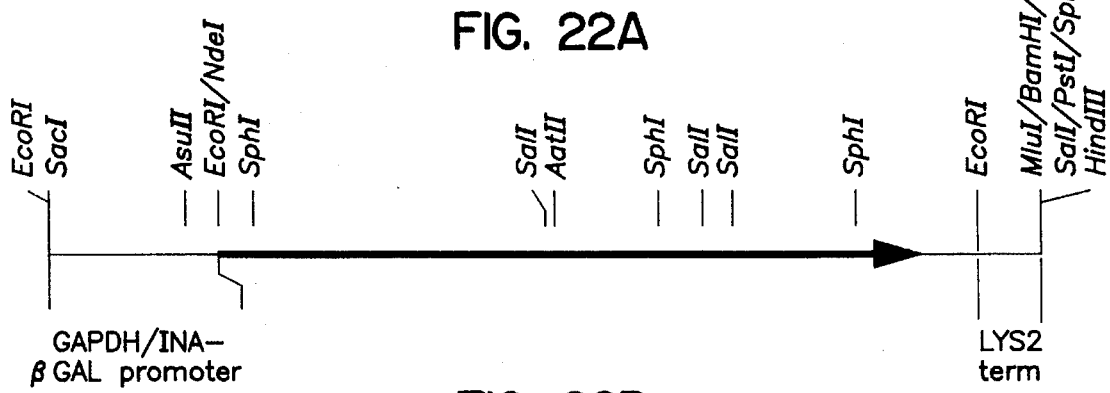
FIG. 22B is a restriction map of ENA-133.

Plasmid pDP133 was digested with the restriction enzymes AsuII and XbaI and the fragments separated on an agarose gel and the 3.5 kb fragment cut out and electro-eluted. Plasmid pSC12vN is a Ciba Geigy construction consisting of the E. coli vector pUG18, the non-inducible erythromycin resistance gene from plasmid pVA838 (F. L Macrina et al., Gene 19, 1982, 345–353) and a Lactococcus lactis plasmid origin of replication, isolated in their laboratories. pSC12vN was digested with the restriction enzymes ClaI and XbaI and treated with alkaline phosphatase to eliminate religation of this vector. The INAZ-βGAL-ENA3 DNA fragment and the ClaI—XbaI digested pSC12vN were mixed together and ligated. This was transformed into E. coli and colonies screened by restriction enzyme analysis and for ice nucleation activity. This identified plasmid pDP135. Plasmids pSC12vN and pDP135 are shown diagrammatically in FIGS. 21 and 22A of the accompanying drawings, in which L. lactis o represents L. lactis plasmid origin of replication. FIG. 22B shows the restriction map of ENA-133 (from pDP133) in which P and T respectively represent promoter and terminator.

Lactococcus lactis strain LM0230 transformation

An overnight culture of L. lactis LM0230 in M17G (M17 medium plus 0.5% glucose) was used for a 1% inoculum into fresh M17G medium. This was grown at 30° C. to an optical density ($OD_{600}$) of approximately 0.4 and the cells pelleted by centrifugation at 10,000 rpm for 5 mins. The supernatant was discarded and the cells resuspended in an equal volume of PS buffer (7 mM Na phosphate pH 6.6, 0.5 molar Sucrose) at 4° C. The cells were again pelleted and finally resuspended in $1/100^{th}$ volume of PS buffer and stored on ice until use (competent cells). Transformation was achieved using a Biorad Gene Pulser™ in conjunction with the Pulse Controller and the Gene Pulser Cuvettes with a 0.2 cm electrode gap. 100 µl of competent cells were mixed with a 1–4 µl volume of DNA in either water or TE buffer and then pipetted into the bottom of the prechilled cuvette. The sample was pulsed at 2000 volts with 400 ohms resistance. The sample was then removed from the cuvette into a sterile microfuge tube and placed on ice. Finally the cells were pelleted in a microfuge for 1 min, resuspended in 300 µl M17G medium and incubated for 1 hr at 30° C. The cells were then plated onto M17G plates supplemented with 4 µg/ml erythromycin and incubated at 30° C. overnight.

Figure 23:
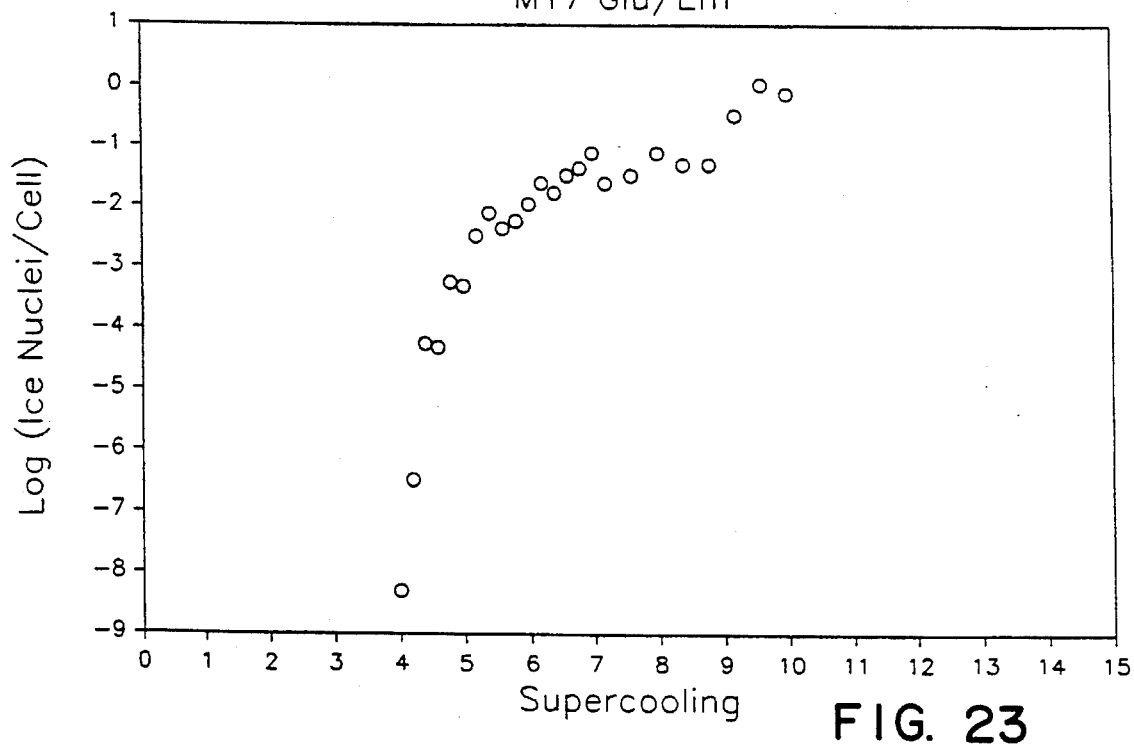
FIG. 23 illustrates the ice nucleating spectra of LMO230+ pDP135.

Plasmid pDP135 was transformed into L. lactis strain LM0230 as described above. Transformants were used to inoculate cultures of M17G medium suplemented with 4 µg/ml erythromycin and incubated at 20° C. with agitation to an $OD_{600}$ of approximately 1.0. These cultures were tested as described and the results plotted. The freezing spectrum of LM0230 plus plasmid pDP135 is shown in FIG. 23 of the accompanying drawings, in which log (ice nuclei/cell) is plotted against supercooling (−°C.).

P-β-Gal promoter

Another more direct approach to the expression of foreign genes in L. lactis is to use the promoter of a known bonafide L. lactis gene. One such published gene is that of the phospho-β-galactosidase gene of strain Z268. The synthesis was as follows;

```
         <        Oligo 220           ><    #          Oligo 221
      5'ttCGAACAACAGTTTGATTAATAAATTTGTAAAAGTTATTTGAGACGAGATCACTCATTCCATTT
      3'aagcTTGTTGTCAAACTAATTATTTAAACATTTTCAATAAACTCTGCTCTAGTGAGTAAGGTAAA
         <                       Oligo 222                              ><
```
```
                                                                      |NdeI
         ><  #                       Oligo 215
      CCTTGGTTTTCAGAACACAGAATCTCGTCTCAAATGCTTTTTTTGAAAGGACTTACACAtatg3'    [SEQ ID NO:21]
      GGAACCAAAAGTCTTGTGTCTTAGAGCAGAGTTTACGAAAAAAACTTTCCTGAATGTGTATag5'   [SEQ ID NO:22]
           Oligo 217                         ><       Oligo 216      >
```

The 6 oligonucleotides were synthesized and purified as usual. 100 pmoles of each oligonucleotide were mixed in a microfuge tube and the 5' phosphates added using the enzyme T4 polynucleotide kinase and [$\gamma$-$^{32}$P]ATP as a phosphate donor. These oligonucleotides were then hybridized to each other as described. Plasmid pJDC9 (J-D.Chen and D. A. Morrison, Gene 64, 1988, 155–164) was digested with the restriction enzymes SacI and HindIII and also treated with alkaline phosphatase. Plasmid pDP108 was digested with the restriction enzymes NdeI and HindIII and the fragments separated on an agarose gel and the 3.85 kb fragment containing the complete ENA3 gene and LYS2 terminator was cut out and electroeluted. This DNA fragment was mixed with the HindIII—SacI digested pJDC9, the oligonucleotide mix and the previously purified SacI—AsuII 600 bp yeast promoter fragment from pK19/GAPDH-dSna and ligated. This was then transformed into competent E. coli cells, expressed for 2 hrs at 37° C. in 500 µl of fresh YT medium, plated onto YT plates supplemented with 100 µg/ml of erythromycin and incubated at 37° C. overnight. Colonies were initially screened by restriction enzyme analysis and for ice nucleation activity, and finally by DNA sequencing. This gave plasmid pDP137 which contains two single base pair deletions within the sequenced promoter (marked by #, see above).

Figure 25:
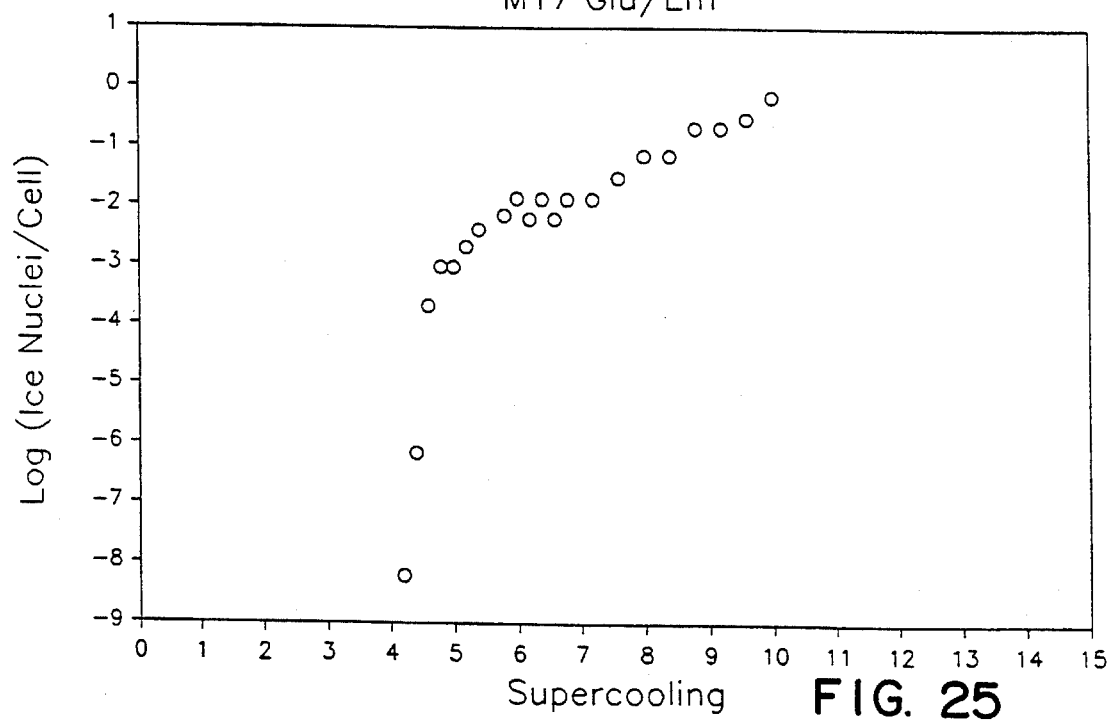
FIG. 25 illustrates the ice nucleating spectra of LMO230+ pDP148.
Figure 24A:
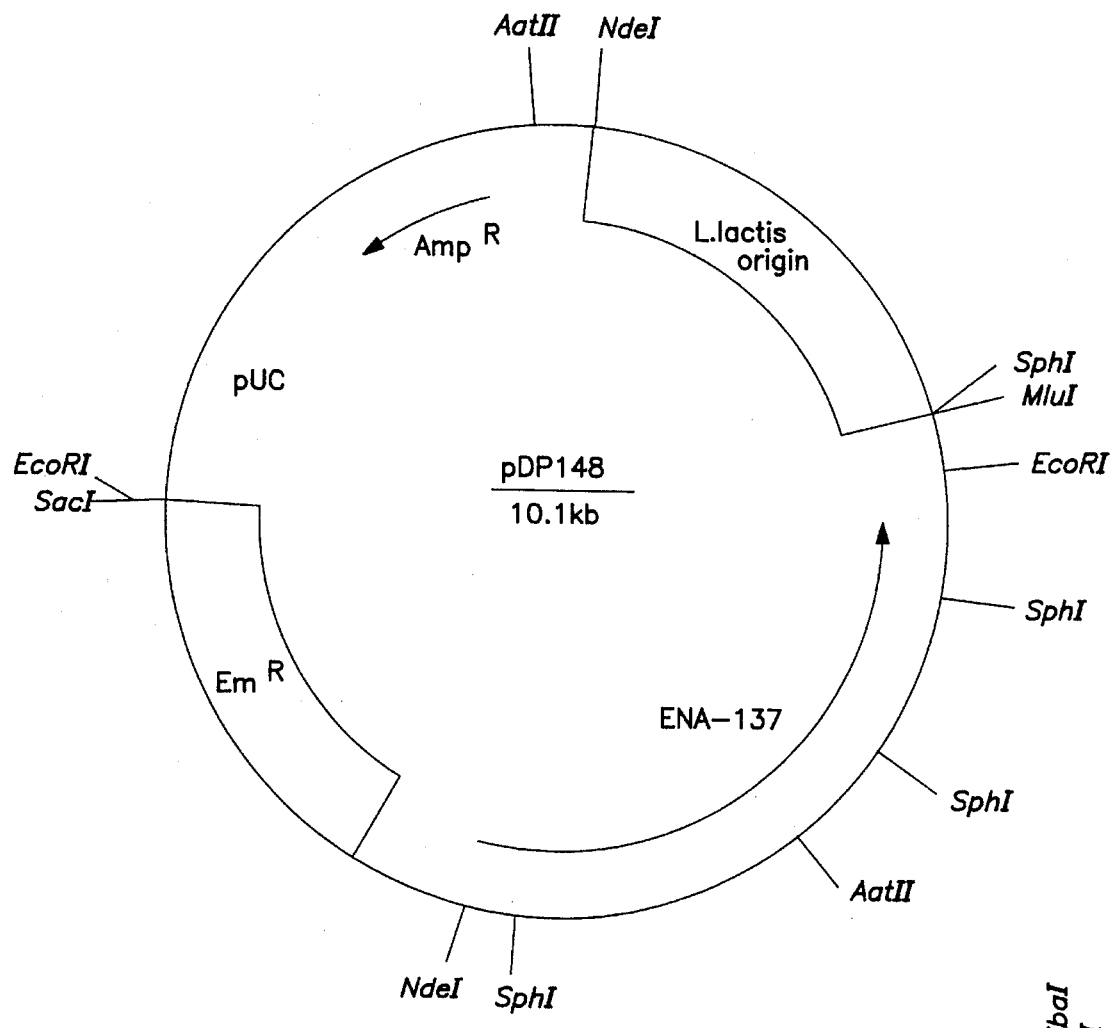
FIG. 24A is a map of the plasmid pDP148.
Figure 24B:
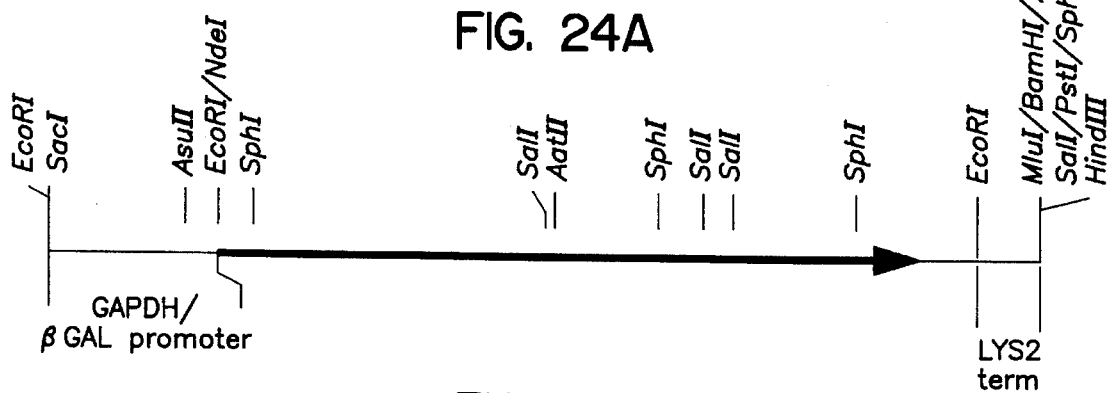
FIG. 24B is a restriction map of ENA-137.

Plasmid pDP137 was digested with the restriction enzymes AsuII and XbaI and the DNA fragments separated on an agarose gel. The 3.95 kb fragment was cut out and the DNA electroeluted. This fragment was mixed with the previously described XbaI—ClaI digested pSC12vN plasmid, ligated and transformed into competent E. coli. Colonies were screened by ice nucleation activity and restriction enzyme analysis to identify the plasmid pDP148 which is shown diagrammatically in FIG. 24A of the accompanying drawings, in which L. lactis o represents L. lactis origin of plasmid replication. FIG. 24B shows a restriction map of ENA-137 (from pDP137) in which P and T respectively represent promoter and terminator. Plasmid pDP148 was transformed into LM0230 as described above. Transformants were used to inoculate cultures of M17G medium supplemented with 4 µg/ml erythromycin and grown at 20° C. with agitation. The freezing spectrum of LM0230 plus plasmid pDP148 is shown in FIG. 25 of the accompanying drawings, in which log (ice nuclei/cell) is plotted against supercooling (−°C.).

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide 17"

( i i i ) HYPOTHETICAL: YES ( x i ) SEQUENCE DESCRIPTION: SEQ ID NO:1:

GCNGCNTAYG GNAGRACNCA RAC                          23

( 2 ) INFORMATION FOR SEQ ID NO:2:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="partial view of the pUC21
            strand carrying a LacZ sequence modified from pUC19"

( i x ) FEATURE:
        ( A ) NAME/KEY: -
        ( B ) LOCATION: 1..48
        ( D ) OTHER INFORMATION: /note="partial view of the pUC19
            strand carrying the lacZ gene"

( i x ) FEATURE:
        ( A ) NAME/KEY: -
        ( B ) LOCATION: 49..88
        ( D ) OTHER INFORMATION: /note="oligonucleotide used to
            create the modified lacZ gene"

( i x ) FEATURE:
        ( A ) NAME/KEY: -
        ( B ) LOCATION: 89..99
        ( D ) OTHER INFORMATION: /note="partial view of the pUC19
            strand carrying the LacZ gene"

( i x ) FEATURE:
        ( A ) NAME/KEY: -
        ( B ) LOCATION: 72..77
        ( D ) OTHER INFORMATION: /note="BglII restriction site used
            to clone the purified 5kb BglII-EcoRI INA5 fragment into
            plasmid pUC21"

( i x ) FEATURE:
        ( A ) NAME/KEY: -
        ( B ) LOCATION: 90..95
        ( D ) OTHER INFORMATION: /note="EcoRI restriction site used
            to clone the purified 5kb BglII-EcoRI INA5 fragment into
            pUC21."

( i x ) FEATURE:
        ( A ) NAME/KEY: CDS
        ( B ) LOCATION: 4..99
        ( D ) OTHER INFORMATION: /partial
            / product="Beta-Galactosidase encoded by pUC21"

( x i ) SEQUENCE DESCRIPTION: SEQ ID NO:2:

```
ATG  ACC  ATG  ATT  ACG  CCA  AGC  TTG  CAT  GCC  TGC  AGG  TGC  ACT  CTA  GAG           48
 Thr  Met  Ile  Thr  Pro  Ser  Leu  His  Ala  Cys  Arg  Cys  Thr  Leu  Glu
```

```
                    1              5                    10                   15
GAT  CCA  CGC  GTG  CCG  GCG  CTA  GCA  GAT  CTC  TCG  AGG  AGC  TCG  AAT  TCA       96
Asp  Pro  Arg  Val  Pro  Ala  Leu  Ala  Asp  Leu  Ser  Arg  Ser  Ser  Asn  Ser
                         20                      25                      30

CTG                                                                                  99
Leu
```

( 2 ) INFORMATION FOR SEQ ID NO:3:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Thr  Met  Ile  Thr  Pro  Ser  Leu  His  Ala  Cys  Arg  Cys  Thr  Leu  Glu  Asp
 1                   5                        10                      15

Pro  Arg  Val  Pro  Ala  Leu  Ala  Asp  Leu  Ser  Arg  Ser  Ser  Asn  Ser  Leu
                    20                        25                      30
```

( 2 ) INFORMATION FOR SEQ ID NO:4:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="partial view of the pUC21
            strand which is complementary to the strand SEQ ID NO:2"

( i x ) FEATURE:
        ( A ) NAME/KEY: -
        ( B ) LOCATION: 16..47
        ( D ) OTHER INFORMATION: /note="synthetic oligonucleotide"

( i x ) FEATURE:
        ( A ) NAME/KEY: -
        ( B ) LOCATION: 1..15
        ( D ) OTHER INFORMATION: /note="partial view of the strand
            which is complementary to the sequence of strand SEQ ID
            NO:2 "

( i x ) FEATURE:
        ( A ) NAME/KEY: -
        ( B ) LOCATION: 48..99
        ( D ) OTHER INFORMATION: /note="partial view of the strand
            which is complementary to the sequence of strand SEQ ID
            NO:2 "

( x i ) SEQUENCE DESCRIPTION: SEQ ID NO:4:

```
CAGTGAATTC  GAGCTCCTCG  AGAGATCTGC  TAGCGCCGGC  ACGCGTGGAT  CCTCTAGAGT       60

GCACCTGCAG  GCATGCAAGC  TTGGCGTATT  CATGGTCAT                                99
```

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="View of the 180bp TaqI-SpHI
            fragment from plasmid EC1 carrying a part of the ENA3
            gene"

( i x ) FEATURE:

( A ) NAME/KEY: -
                    ( B ) LOCATION: 9..11
                    ( D ) OTHER INFORMATION: /note="TaqI restriction site used
                            to digest plasmid EC1. The SphI restriction site is not
                            shown."

( x i ) SEQUENCE DESCRIPTION: SEQ ID NO:5:

ATGCTGTAAT GAATATCGAC AAA 23

( 2 ) INFORMATION FOR SEQ ID NO:6:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( i i ) MOLECULE TYPE: other nucleic acid
                    ( A ) DESCRIPTION: /desc ="oligonucleotide 124"

( i x ) FEATURE:
                    ( A ) NAME/KEY: -
                    ( B ) LOCATION: 1..5
                    ( D ) OTHER INFORMATION: /note="EcoRI restriction site"

( i x ) FEATURE:
                    ( A ) NAME/KEY: -
                    ( B ) LOCATION: 5..10
                    ( D ) OTHER INFORMATION: /note="NdeI restriction site"

( x i ) SEQUENCE DESCRIPTION: SEQ ID NO:6:

AATTCATATG AATAT 15

( 2 ) INFORMATION FOR SEQ ID NO:7:

( i ) SEQUENCE CHARACTERISTICS:
                    ( A ) LENGTH: 13 base pairs
                    ( B ) TYPE: nucleic acid
                    ( C ) STRANDEDNESS: single
                    ( D ) TOPOLOGY: linear ( i i ) MOLECULE TYPE: other nucleic acid
                    ( A ) DESCRIPTION: /desc ="oligonucleotide 125"

( x i ) SEQUENCE DESCRIPTION: SEQ ID NO:7:

CGATATTCAT ATG 13

( 2 ) INFORMATION FOR SEQ ID NO:8:

( i ) SEQUENCE CHARACTERISTICS:
                    ( A ) LENGTH: 49 base pairs
                    ( B ) TYPE: nucleic acid
                    ( C ) STRANDEDNESS: single
                    ( D ) TOPOLOGY: linear ( i i ) MOLECULE TYPE: other nucleic acid
                    ( A ) DESCRIPTION: /desc ="partial view of the pDP110
                            strand which carry a GAPDH promoter linked to the ENA3
                            gene with the oligonucleotide linker 141"

( i x ) FEATURE:
                    ( A ) NAME/KEY: -
                    ( B ) LOCATION: 1..2
                    ( D ) OTHER INFORMATION: /note="3'nucleotide view of the
                            strand carrying the GAPDH promoter from pK19/GAPDH-dSsp"

( i x ) FEATURE:
                    ( A ) NAME/KEY: -
                    ( B ) LOCATION: 3..39
                    ( D ) OTHER INFORMATION: /note="oligonucleotide 141"

( i x ) FEATURE:
                    ( A ) NAME/KEY: -
                    ( B ) LOCATION: 40..49

(D) OTHER INFORMATION: /note="5'nucleotide view of the
strand carrying the ENA3 gene from plasmid pDP108"

(ix) FEATURE:
(A) NAME/KEY: -
(B) LOCATION: 1..5
(D) OTHER INFORMATION: /note="AsuII restriction site used
to ligate the GAPDH promoter to oligonucleotides 141 and
142"

(ix) FEATURE:
(A) NAME/KEY: -
(B) LOCATION: 39..44
(D) OTHER INFORMATION: /note="EcoRI restriction site used
to ligate the ENA3 gene to oligonucleotides 141 and 142"

(xi) SEQUENCE DESCRIPTION: SEQ ID NO:8:

TTCGAATTTT TGAGTTATCG AGATTTTCAG GAGCTAAGGA ATTCATATG    49

(2) INFORMATION FOR SEQ ID NO:9:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="partial view of the pDP108
strand which is complementary to the strand SEQ ID NO:8"

(ix) FEATURE:
(A) NAME/KEY: -
(B) LOCATION: 1..6
(D) OTHER INFORMATION: /note="3'nucleotides view of a
strand of the ENA3 gene from plasmid pDP108"

(ix) FEATURE:
(A) NAME/KEY: -
(B) LOCATION: 7..44
(D) OTHER INFORMATION: /note="oligonucleotide 142"

(ix) FEATURE:
(A) NAME/KEY: -
(B) LOCATION: 45..48
(D) OTHER INFORMATION: /note="5'nucleotide view of a
strand of the GAPDH promoter from plasmid
pK19/GAPDH- dSsp"

(xi) SEQUENCE DESCRIPTION: SEQ ID NO:9:

CATATGAATT CCTTAGCTCC TGAAAATCTC GATAACTAAA AATTCGAA    48

(2) INFORMATION FOR SEQ ID NO:10:

(i) SEQUENCE CHARACTERISTICS:
(A) LENGTH: 34 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: -
(B) LOCATION: 14..19
(D) OTHER INFORMATION: /note="EcoRV restriction site"

(xi) SEQUENCE DESCRIPTION: SEQ ID NO:10:

ACTTTAACTA ATAGATTATG CAGATTTTCG TCAA    34

(2) INFORMATION FOR SEQ ID NO:11:

(i) SEQUENCE CHARACTERISTICS:
(A) LENGTH: 25 base pairs (B) TYPE: nucleic acid
(C) STRANDEDNESS: single
(D) TOPOLOGY: linear (ii) MOLECULE TYPE: other nucleic acid
(A) DESCRIPTION: /desc ="oligonucleotide 166"

(ix) FEATURE:
(A) NAME/KEY: -
(B) LOCATION: 12..17
(D) OTHER INFORMATION: /note="EcoRV restriction site introduced by in-vitro mutagenesis in UBI4 promoter between bases 14 and 19 of Seq ID NO:10"

(xi) SEQUENCE DESCRIPTION: SEQ ID NO:11:

```
GCTTTTAGAC GCTATAGATA ATCAA                                    25
```

(2) INFORMATION FOR SEQ ID NO:12:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="hypothetical introduction into the encoding strand of a pDP111 fragment carrying the ENA3 gene of the oligonucleotide 174 carrying the PHO5 signal"

(ix) FEATURE:
(A) NAME/KEY: -
(B) LOCATION: one-of(1)..1
(D) OTHER INFORMATION: /note="3'nucleotide view of a strand of the 700bp SacI-EcoRI fragment from plasmid pDP111 "

(ix) FEATURE:
(A) NAME/KEY: -
(B) LOCATION: 2..60
(D) OTHER INFORMATION: /note="oligonucleotide 174"

(ix) FEATURE:
(A) NAME/KEY: -
(B) LOCATION: 61..64
(D) OTHER INFORMATION: /note="5'nucleotides view of a strand of the 1.45kb NdeI-AatII fragment from pDP111"

(ix) FEATURE:
(A) NAME/KEY: -
(B) LOCATION: 1..6
(D) OTHER INFORMATION: /note="EcoRI restriction site used to ligate the 700bp SacI-EcoRI fragment of pDP111 to oligonucleotides 174 and 175"

(ix) FEATURE:
(A) NAME/KEY: CDS
(B) LOCATION: 8..64
(D) OTHER INFORMATION: /product="ENA3 peptide fused to PHO5 signal sequence"

(xi) SEQUENCE DESCRIPTION: SEQ ID NO:12:

```
GAATTCA ATG TTT AAA TCT GTT GTT TAT TCA ATT TTA GCC GCT TCT TTG    49
        Met Phe Lys Ser Val Val Tyr Ser Ile Leu Ala Ala Ser Leu
                 35              40                  45

GCC AAT GCA GGT ATG                                                64
Ala Asn Ala Gly Met
             50
```

(2) INFORMATION FOR SEQ ID NO:13:

(i) SEQUENCE CHARACTERISTICS:
(A) LENGTH: 19 amino acids
(B) TYPE: amino acid (D) TOPOLOGY: linear (ii) MOLECULE TYPE: protein (xi) SEQUENCE DESCRIPTION: SEQ ID NO:13:

| Met | Phe | Lys | Ser | Val | Val | Tyr | Ser | Ile | Leu | Ala | Ala | Ser | Leu | Ala | Asn |
|---|---|---|---|---|---|---|---|---|---|---|---|---|---|---|---|
| 1 | | | | 5 | | | | | 10 | | | | | 15 | |

Ala Gly Met (2) INFORMATION FOR SEQ ID NO:14:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="sequence which is
            complementary to SEQ ID NO:12"

(ix) FEATURE:
        (A) NAME/KEY: -
        (B) LOCATION: 1..2
        (D) OTHER INFORMATION: /note="5'nucleotides view of a
            strand of the 1.45kb NdeI-AatII fragment from pDP111 "

(ix) FEATURE:
        (A) NAME/KEY: -
        (B) LOCATION: 3..59
        (D) OTHER INFORMATION: /note="oligonucleotide 175"

(ix) FEATURE:
        (A) NAME/KEY: -
        (B) LOCATION: 60..64
        (D) OTHER INFORMATION: /note="3'nucleotides view of a
            strand of the 700bp SacI-EcoRI fragment from pDP111"

(xi) SEQUENCE DESCRIPTION: SEQ ID NO:14:

```
CATACCTGCA TTGGCAAAG AAGCGGCTAA AATTGAATAA ACAACAGATT TAAACATTGA       60

ATTC                                                                   64
```

(2) INFORMATION FOR SEQ ID NO:15:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Cleavage-site
        (B) LOCATION: 0..1

(ix) FEATURE:
        (A) NAME/KEY: Peptide
        (B) LOCATION: -25..0
        (D) OTHER INFORMATION: /note="PHO5 signal peptide
            duplicated"

(ix) FEATURE:
        (A) NAME/KEY: Protein
        (B) LOCATION: 26..one-of(27)
        (D) OTHER INFORMATION: /note="ENA3 protein"

(xi) SEQUENCE DESCRIPTION: SEQ ID NO:15:

| Met | Phe | Lys | Ser | Val | Val | Tyr | Ser | Met | Phe | Lys | Ser | Val | Val | Tyr | Ser |
|---|---|---|---|---|---|---|---|---|---|---|---|---|---|---|---|
| 1 | | | | 5 | | | | | 10 | | | | | 15 | |

| Ile | Leu | Ala | Ala | Ser | Leu | Ala | Asn | Ala | Gly | Met |
|---|---|---|---|---|---|---|---|---|---|---|
| | | | 20 | | | | | 25 | | |

(2) INFORMATION FOR SEQ ID NO:16:

(i) SEQUENCE CHARACTERISTICS:
        (A) LENGTH: 47 base pairs
        (B) TYPE: nucleic acid
        (C) STRANDEDNESS: Not Relevant
        (D) TOPOLOGY: Not Relevant (ii) MOLECULE TYPE: other nucleic acid
        (A) DESCRIPTION: /desc ="partial view of the plasmid
            pUC19/CPY(p- p) strand carrying the CPY pre-pro peptide"

(ix) FEATURE:
        (A) NAME/KEY: -
        (B) LOCATION: one-of(1)..1
        (D) OTHER INFORMATION: /note="3'nucleotides view of the
            strand of the EcoRI-HindIII fragment from pUC19 which
            carry the GAPDH/CAT promoter"

(ix) FEATURE:
        (A) NAME/KEY: -
        (B) LOCATION: 2..43
        (D) OTHER INFORMATION: /note="oligonucleotide 206"

(ix) FEATURE:
        (A) NAME/KEY: -
        (B) LOCATION: 44..47
        (D) OTHER INFORMATION: /note="5'nucleotides view of the
            strand of the 800bp HindIII-StuI fragment from
            pBR322/PHO5- pre-pro-CPY which carry the sequence encoding
            the CPY pre- pro peptide"

(ix) FEATURE:
        (A) NAME/KEY: -
        (B) LOCATION: 1..6
        (D) OTHER INFORMATION: /note="EcoRI restriction site"

(ix) FEATURE:
        (A) NAME/KEY: -
        (B) LOCATION: 41..46
        (D) OTHER INFORMATION: /note="StuI restriction site"

(ix) FEATURE:
        (A) NAME/KEY: CDS
        (B) LOCATION: 9..47
        (D) OTHER INFORMATION: /product="CPY pre-pro peptide"

(xi) SEQUENCE DESCRIPTION: SEQ ID NO:16:

```
GAATTCAT ATG AAA GCA TTC ACC AGT TTA CTA TGT GGA CTA GGC CTG        47
         Met Lys Ala Phe Thr Ser Leu Leu Cys Gly Leu Gly Leu
         20              25                  30
```

(2) INFORMATION FOR SEQ ID NO:17:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:17:

```
Met Lys Ala Phe Thr Ser Leu Leu Cys Gly Leu Gly Leu
 1               5                   10
```

(2) INFORMATION FOR SEQ ID NO:18:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid ( A ) DESCRIPTION: /desc ="sequence which is
complementary to SEQ ID NO:16"

( i x ) FEATURE:
( A ) NAME/KEY: -
( B ) LOCATION: 1..4
( D ) OTHER INFORMATION: /note="3'nucleotides view of a
strand of the 800bp HindIII-StuI fragment"

( i x ) FEATURE:
( A ) NAME/KEY: -
( B ) LOCATION: 5..42
( D ) OTHER INFORMATION: /note="oligonucleotide 207"

( i x ) FEATURE:
( A ) NAME/KEY: -
( B ) LOCATION: 43..47
( D ) OTHER INFORMATION: /note="5'nucleotides view of a
strand of the EcoRI-HindIII fragment from pUC19 "

( x i ) SEQUENCE DESCRIPTION: SEQ ID NO:18:

CAGGCCTAGT CCACATAGTA AACTGGTGAA TGCTTTCATA TGAATTC       47

( 2 ) INFORMATION FOR SEQ ID NO:19:

( i ) SEQUENCE CHARACTERISTICS:
( A ) LENGTH: 120 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="Partial view of the pDP133
strand which carry a hybrid promoter based on the ENA3
promoter and the potential leader from the phospho-
beta- galactosidase promoter"

( i x ) FEATURE:
( A ) NAME/KEY: -
( B ) LOCATION: 1..2
( D ) OTHER INFORMATION: /note="3'nucleotides view of the
strand of the 600bp SacI-AsuII fragment from
pK19/GAPDH- dSna which carry a yeast promoter"

( i x ) FEATURE:
( A ) NAME/KEY: -
( B ) LOCATION: 3..45
( D ) OTHER INFORMATION: /note="oligonucleotide 186"

( i x ) FEATURE:
( A ) NAME/KEY: -
( B ) LOCATION: 46..67
( D ) OTHER INFORMATION: /note="oligonucleotide 214"

( i x ) FEATURE:
( A ) NAME/KEY: -
( B ) LOCATION: 68..116
( D ) OTHER INFORMATION: /note="oligonucleotide 215"

( i x ) FEATURE:
( A ) NAME/KEY: -
( B ) LOCATION: 117..120
( D ) OTHER INFORMATION: /note="5'nucleotides view of the
strand of the 1.5kb NdeI-AatII fragment from pDP108 which
carry the EN3 gene"

( i x ) FEATURE:
( A ) NAME/KEY: -
( B ) LOCATION: 1..6
( D ) OTHER INFORMATION: /note="AsuII restriction site used
to ligate the 600 bp SacI-AsuII fragment from
pK19/GAPDH- dSna to oligonucleotides 186 and 187"

( i x ) FEATURE:
( A ) NAME/KEY: -
( B ) LOCATION: 115..120
( D ) OTHER INFORMATION: /note="NdeI restriction site used
to ligate the 4.5kb NdeI-AatII fragment from pDP108 to oligonucleotides 215 and 216"

( x i ) SEQUENCE DESCRIPTION: SEQ ID NO:19:

| | | | | | |
|---|---|---|---|---|---|
| TTCGAATGCT | TGATAAGTGC | GCTGCTTTTA | TTTAAAGGAT | CTAGGAATTT | TCCATTTCCT | 60 |
| TGGTTTTCAG | AACACAGAAT | CTCGTCTCAA | ATGCTTTTTT | TGAAAGGACT | TACACATATG | 120 |

( 2 ) INFORMATION FOR SEQ ID NO:20:

( i ) SEQUENCE CHARACTERISTICS:
    ( A ) LENGTH: 120 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="sequence which is
      complementary to SEQ ID NO:19"

( i x ) FEATURE:
    ( A ) NAME/KEY: -
    ( B ) LOCATION: 1..2
    ( D ) OTHER INFORMATION: /note="3'nucleotides view of a
      strand of the 1.5kb NdeI-AatII fragment from pDP108"

( i x ) FEATURE:
    ( A ) NAME/KEY: -
    ( B ) LOCATION: 3..26
    ( D ) OTHER INFORMATION: /note="oligonucleotide 216"

( i x ) FEATURE:
    ( A ) NAME/KEY: -
    ( B ) LOCATION: 27..71
    ( D ) OTHER INFORMATION: /note="oligonucleotide 217"

( i x ) FEATURE:
    ( A ) NAME/KEY: -
    ( B ) LOCATION: 72..116
    ( D ) OTHER INFORMATION: /note="oligonucleotide 187"

( i x ) FEATURE:
    ( A ) NAME/KEY: -
    ( B ) LOCATION: 117..120
    ( D ) OTHER INFORMATION: /note="5'nucleotides view of a
      strand of the 600bp SacI-AsuII fragment from
      pK19/GAPDH- dSsna "

( x i ) SEQUENCE DESCRIPTION: SEQ ID NO:20:

| | | | | | |
|---|---|---|---|---|---|
| CATATGTGTA | AGTCCTTTCA | AAAAAAGCAT | TTGAGATGAG | ATTCTGTGTT | CTGAAAACCA | 60 |
| AGGAAATGGA | AAATTCCTAG | ATCCTTTAAA | TAAAAGCAGC | GCACTTATCA | AGCATTCGAA | 120 |

( 2 ) INFORMATION FOR SEQ ID NO:21:

( i ) SEQUENCE CHARACTERISTICS:
    ( A ) LENGTH: 128 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="Partial view of the pDP137
      strand which carry a promoter of a L.lactis gene isolated
      from plasmid pJDC9"

( i x ) FEATURE:
    ( A ) NAME/KEY: -
    ( B ) LOCATION: 1..2
    ( D ) OTHER INFORMATION: /note="3'nucleotides view of the
      strand of the 600bp SacI-AsuII fragment from
      pK19/GAPDH- dSna which carry a yeast promoter"

( i x ) FEATURE:
    ( A ) NAME/KEY: -
    ( B ) LOCATION: 3..25
    ( D ) OTHER INFORMATION: /note="oligonucleotide 220"

( i x ) FEATURE:
    ( A ) NAME/KEY: -
    ( B ) LOCATION: 26..75
    ( D ) OTHER INFORMATION: /note="oligonucleotide 221"

( i x ) FEATURE:
    ( A ) NAME/KEY: -
    ( B ) LOCATION: 76..124
    ( D ) OTHER INFORMATION: /note="oligonucleotide 215"

( i x ) FEATURE:
    ( A ) NAME/KEY: -
    ( B ) LOCATION: 125..128
    ( D ) OTHER INFORMATION: /note="5'nucleotides view of the strand of the 3.85kb NdeI-HindIII fragment from pDP108 which carry the ENA3 protein"

( i x ) FEATURE:
    ( A ) NAME/KEY: -
    ( B ) LOCATION: one-of(1)..3
    ( D ) OTHER INFORMATION: /note="AsuII restriction site used to ligate oligonucleotides 220 and 222"

( i x ) FEATURE:
    ( A ) NAME/KEY: -
    ( B ) LOCATION: 124..128
    ( D ) OTHER INFORMATION: /note="NdeI restriction site used to ligate oligonucleotides 215 and 216"

( x i ) SEQUENCE DESCRIPTION: SEQ ID NO:21:

```
TTCGAACAAC AGTTTGATTA ATAAATTTGT AAAAGTTATT TGAGACGAGA TCACTCATTC        60

CATTTCCTTG GTTTTCAGAA CACAGAATCT CGTCTCAAAT GCTTTTTTG  AAAGGACTTA       120

CACATATG                                                                128
```

( 2 ) INFORMATION FOR SEQ ID NO:22:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence which is complementary to SEQ ID NO:21"

( i x ) FEATURE:
        ( A ) NAME/KEY: -
        ( B ) LOCATION: 1..2
        ( D ) OTHER INFORMATION: /note="3'nucleotides view of a strand of the 3.85kb NdeI-HindII fragment of pDP108 "

( i x ) FEATURE:
        ( A ) NAME/KEY: -
        ( B ) LOCATION: 3..26
        ( D ) OTHER INFORMATION: /note="oligonucleotide 216"

( i x ) FEATURE:
        ( A ) NAME/KEY: -
        ( B ) LOCATION: 27..71
        ( D ) OTHER INFORMATION: /note="oligonucleotide 217"

( i x ) FEATURE:
        ( A ) NAME/KEY: -
        ( B ) LOCATION: 72..124
        ( D ) OTHER INFORMATION: /note="oligonucleotide 222"

( i x ) FEATURE:
        ( A ) NAME/KEY: -
        ( B ) LOCATION: 125..128
        ( D ) OTHER INFORMATION: /note="5'nucleotides view of a strand of the 600bp SacI-AsuII fragment from pK19/GAPDH- dSna "

( x i ) SEQUENCE DESCRIPTION: SEQ ID NO:22:

```
GATATGTGTA AGTCCTTTCA AAAAAAGCAT TTGAGACGAG ATTCTGTGTT CTGAAAACCA        60

AGGAAATGGA ATGAGTGATC TCGTCTCAAA TAACTTTTAC AAATTTATTA ATCAAACTGT       120

TGTTCGAA                                                                128
```

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:23:

```
Ala  Gly  Tyr  Gly  Ser  Thr  Gln  Thr
 1                    5
```

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="view of one strand of the
            180bp TaqI- SpHI fragment which is complementary to the
            strand SEQ ID NO:5"

( i x ) FEATURE:
        ( A ) NAME/KEY: -
        ( B ) LOCATION: 13..15
        ( D ) OTHER INFORMATION: /note="TaqI restriction site"

( x i ) SEQUENCE DESCRIPTION: SEQ ID NO:24:

```
TTTGTCGATA TTCATTACAG CAT                                                23
```

We claim:

1. The *S.cerevisiae* strain NCIMB40215 transformed with the plasmid pDP143.

2. The plasmid pDP143.

* * * * *